US012788751B2

(12) United States Patent
Lim et al.

(10) Patent No.: US 12,788,751 B2
(45) Date of Patent: Nov. 10, 2026

(54) TOLL-LIKE RECEPTOR 7 OR 8 AGONIST-CHOLESTEROL COMPLEX AND METHOD OF PREPARING SAME

(71) Applicant: PROGENEER, INC., Seoul (KR)

(72) Inventors: Yong Taik Lim, Seongnam-si (KR); Hong Sik Shin, Anyang-si (KR); Long Ren, Suwon-si (KR)

(73) Assignee: PROGENEER, INC., Seoul (KR)

( * ) Notice: Subject to any disclaimer, the term of this patent is extended or adjusted under 35 U.S.C. 154(b) by 1186 days.

(21) Appl. No.: 17/391,224

(22) Filed: Aug. 2, 2021

(65) Prior Publication Data

US 2022/0008411 A1 Jan. 13, 2022

Related U.S. Application Data

(63) Continuation of application No. PCT/KR2020/001753, filed on Feb. 7, 2020.

(30) Foreign Application Priority Data

Feb. 8, 2019 (KR) ........................ 10-2019-0014756
Feb. 7, 2020 (KR) ........................ 10-2020-0014775

(51) Int. Cl.

| | |
|---|---|
| ***A61K 31/4745*** | (2006.01) |
| ***A61K 39/39*** | (2006.01) |
| ***A61K 47/54*** | (2017.01) |
| ***A61K 47/69*** | (2017.01) |
| *A61K 39/00* | (2006.01) |

(52) U.S. Cl.

CPC .......... *A61K 31/4745* (2013.01); *A61K 39/39* (2013.01); *A61K 47/54* (2017.08); *A61K 47/6907* (2017.08); *A61K 47/6911* (2017.08); *A61K 2039/55555* (2013.01)

(58) Field of Classification Search

CPC .... A61K 31/4745; A61K 39/39; A61K 47/54; A61K 47/6907; A61K 47/6911; A61K 2039/55555

See application file for complete search history.

(56) References Cited

U.S. PATENT DOCUMENTS

2012/0294885 A1 11/2012 David et al.
2013/0336996 A1 12/2013 Vernejoul et al.
(Continued)

FOREIGN PATENT DOCUMENTS

EP 2 674 170 A1 12/2013
JP 2013-525450 A 6/2013
WO WO-2017102654 A1 * 6/2017 ............. A61P 37/04
(Continued)

OTHER PUBLICATIONS

Hennessy et al. Targeting Toll-like receptors: emerging therapeutics 48 . Nat Rev Drug Discov 9, 293-307 (2010). (Year: 2010).*
(Continued)

*Primary Examiner* — Matthew P Coughlin
*Assistant Examiner* — Ashli A Chicks
(74) *Attorney, Agent, or Firm* — NSIP Law

(57) ABSTRACT

The present disclosure relates to a toll-like receptor 7/8 agonist-cholesterol complex comprising: a cholesterol; and a toll-like receptor 7/8 agonist, wherein the cholesterol is linked to an active site of the toll-like receptor 7/8 agonist.

14 Claims, 28 Drawing Sheets

(56) References Cited

U.S. PATENT DOCUMENTS

| | | | |
|---|---|---|---|
| 2018/0273560 A1 | 9/2018 | Bazin-Lee et al. |
| 2018/0362560 A1 | 12/2018 | Bazin-Lee et al. |

FOREIGN PATENT DOCUMENTS

| | | |
|---|---|---|
| WO | WO 2018/147710 A1 | 8/2018 |
| WO | WO 2018/232257 A1 | 12/2018 |

OTHER PUBLICATIONS

Kang et al. ACS Appl. Mater. Interfaces 2019, 11, 36371-36382. (Year: 2019).*

Irby et al. Mol. Pharmaceutics 2017, 14, 1325-1338. (Year: 2017).*

Ansell et al. J. Med. Chem. 2008, 51, 3288-3296. (Year: 2008).*

Chi et al. (2017) Anti-tumor Activity of Toll-Like Receptor 7 Agonists. Front. Pharmacol. 8:304. (Year: 2017).*

David J Dowling, Recent Advances in the Discovery and Delivery of TLR7/8 Agonists as Vaccine Adjuvants, ImmunoHorizons, vol. 2, Issue 6, Jul. 2018, pp. 185-197. (Year: 2018).*

Sato-Kaneko, Fumi, et al. "Combination immunotherapy with TLR agonists and checkpoint inhibitors suppresses head and neck cancer." *JCI insight* 2.18 (Sep. 21, 2017). pp.1-18.

Zhao, By Gan, et al. "Combination therapy targeting toll like receptors 7, 8 and 9 eliminates large established tumors." *Journal for immunotherapy of cancer* 2.1 (Feb. 1, 2012): pp. 1-10.

Reed, Steven G., Mark T. Orr, and Christopher B. Fox. "Key roles of adjuvants in modern vaccines." *Nature medicine* 19.12 (Dec. 5, 2013): pp. 1597-1608.

Wilkinson, Alexander, et al. "Lipid conjugation of TLR7 agonist Resiquimod ensures co-delivery with the liposomal Cationic Adjuvant Formulation 01 (CAF01) but does not enhance immunopotentiation compared to non-conjugated Resiquimod+ CAF01." *Journal of Controlled Release* 291 (Dec. 10, 2018): pp. 1-10.

Zhu, Jiang, et al. "Local administration of a novel Toll-like receptor 7 agonist in combination with doxorubicin induces durable tumouricidal effects in a murine model of T cell lymphoma." *Journal of hematology & oncology* 8.1 (2015): pp. 1-10.

Mahato, Rubi, Wanyi Tai, and Kun Cheng. "Prodrugs for improving tumor targetability and efficiency." *Advanced drug delivery reviews* 63.8 (Jul. 18, 2011): pp. 659-670.

Zhang, Zhikuan, et al. "Structural analyses of toll-like receptor 7 reveal detailed RNA sequence specificity and recognition mechanism of agonistic ligands." *Cell reports* 25.12 (Dec. 18, 2018): pp. 3371-3381.

Gao, Dong, et al. "Synergy of purine-scaffold TLR7 agonist with doxorubicin on systemic inhibition of lymphoma in mouse model." *Journal of Cancer* 8.16 (Sep. 15, 2017): pp. 3183-3189.

Ignacio, Bob J., et al. "Toll-like receptor agonist conjugation: a chemical perspective." *Bioconjugate chemistry* 29.3 (Jan. 29, 2018): pp. 587-603.

Salazar, Lupe G., et al. "Topical imiquimod plus nab-paclitaxel for breast cancer cutaneous metastases: a phase 2 clinical trial." *JAMA oncology* 3.7 (Jul. 2017): pp. 969-973.

Extended European search report issued on Jan. 5, 2023, in counterpart European Patent Application No. 20753017.1 (9 pages in English).

Ignacio, Bob J., et al., "Toll-like receptor agonist conjugation: a chemical perspective," *Bioconjugate chemistry*, 29, 3, 2018 (pp. 587-603).

Wilkinson, Alexander, et al., "Lipid conjugation of TLR7 agonist Resiquimod ensures co- delivery with the liposomal Cationic Adjuvant Formulation 01 (CAF01) but does not enhance immunopotentiation compared to non-conjugated Resiquimod+ CAF01," *Journal of Controlled Release*, 291, 2018 (pp. 1-10).

International Search Report issued on Jun. 19, 2020 in counterpart International Patent application No. PCT/KR2020/001753 (3 pages in English and 3 pages in Korean).

* cited by examiner 2-3 $^{15}$N-HSQC result of Resiquimod

Expected product
CR4
$^{15}$N-HSQC

FIG. 24

| TEST GROUP | Tumor volume ($mm^3$) | Tumor free mice (number) |
|---|---|---|
| PBS | 1,300 ± 145 | 0/10 |
| Doxorubicin | 990 ± 46 | 0/10 |
| Paclitaxel | 900 ± 51 | 0/10 |
| Doxorubicin + Lipo(Chol-848) | <100 | 3/10 |
| Paclitaxel + Lipo(Chol-848) | <115 | 3/10 |

TOLL-LIKE RECEPTOR 7 OR 8 AGONIST-CHOLESTEROL COMPLEX AND METHOD OF PREPARING SAME

CROSS-REFERENCE TO RELATED APPLICATIONS

Pursuant to 35 USC 120 and 365(c), this application is a continuation of International Application No. PCT/KR2020/001753 filed on Feb. 7, 2020, and claims the benefit under 35 USC 119(a) of Korean Patent Application No. 10-2019-0014756 filed on Feb. 8, 2019 and Korean Patent Application No. 10-2020-0014775 filed on Feb. 7, 2020, in the Korean Intellectual Property Office, the entire disclosures of which are incorporated herein by reference for all purposes.

BACKGROUND

1. Field

The present disclosure relates to a toll-like receptor 7/8 agonist-cholesterol complex, and more particularly, to a complex, in which a cholesterol is linked to an active site of a toll-like receptor 7/8 agonist by means of a chemical bond with a cleavable site, and a method of preparing the same.

2. Description of Background

An immune response is a series of responses of activated immune cells against exogenous and endogenous materials, that is, antigens, and when microorganisms such as bacteria or viruses, or foreign bio-substances are introduced into a body, they are recognized by immune cells, which are then activated to secrete a factor such as a cytokine, thereby causing an inflammatory response. Recently, active research on mechanisms in an innate immune response stage that non-specifically acts at the early stage of infection is actively progressing, and among these mechanisms, a toll-like receptor (TLR), which is a gene capable of recognizing a pathogen in an early stage of inflammation, is known to recognize a cell membrane component of a pathogen or a nucleic acid component to induce an immune response, and by using the TLR, studies on various toll-like receptor ligands for activating immune cells are actively progressing.

Among these ligands, a toll-like receptor 7/8 agonist-based material is used as an adjuvant inducing a cellular immune response, and may be imiquimod, resiquimod, dactolisib, gardiquimod, sumanirole, motolimod, vesatolimod, loxoribine, SM360320, CL264, 3M-003, IMDQ, or Compound 54 (US 2012-0294885 A1). The toll-like receptor 7/8 agonist is a toll-like receptor 7/8 agonist in an endosome and known to effectively induce not only humoral immunity but also cellular immunity. However, the toll-like receptor 7/8 agonist has difficulty in being dispersed in an aqueous solution due to its molecular structure. In addition, since such agonist is dissolved only in a special organic solvent such as DMSO or methanol, but is not dissolved in a generally used organic solvent, there is a limitation in preparing various forms of immune activation materials. Therefore, the agonist is commercially used in a cream-type formulation (e.g., Aldara® cream), in which various surfactants are mixed. In some studies, to overcome such a problem, while being prepared in the form of a salt to be dissolved in an aqueous solution, the toll-like receptor 7/8 agonist prepared in a salt form is absorbed into a blood vessel in a body to induce a systemic immune response in a blood vessel, thereby causing many side effects (e.g., cytokine storm, and various non-specific hypersensitivity immune responses). For this reason, the salt-form toll-like receptor 7/8 agonist described above is difficult to use. Due to these side effects, in order to actually use it for treatment, it is necessary to be treated at a lower concentration than an effective dose, and thus may become a cause of reduced efficiency. In some pharmaceutical companies, to overcome such problems, an attempt to prevent direct absorption into a blood vessel by introducing a lipid showing a lipophilic property or directly chemically binding to a polymer chain with a huge size is also being made. However, since the active site of a toll-like receptor 7/8 agonist prepared by the above-mentioned is still exposed to the outside, it still has a potential to cause toxicity by inducing a non-specific immune response in the body.

Accordingly, if a toll-like receptor 7/8 agonist, which is not absorbed into a blood vessel in a body and can be prepared in various forms in which a non-specific immune response is suppressed, is developed, it is expected to be widely used as various immune activating agents with low side effects.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, the toll-like receptor 7/8 agonist-cholesterol complex includes: a cholesterol; and a toll-like receptor 7/8 agonist, wherein the cholesterol is linked to an active site of the toll-like receptor 7/8 agonist.

The cholesterol may be linked to the active site of the toll-like receptor 7/8 agonist by a separable linkage.

The separable linkage may be a cleavable chemical bond selected from the group consisting of a carbamate, a disulfide, an ester, a peptide and an azide.

The toll-like receptor 7/8 agonist may be selected from the group consisting of an imidazoquinoline-based agonist, a hydroxyadenine-based agonist, a pteridone-based agonist, an aminopyrimidine-based agonist, a benzoazepine-based agonist, a thia-oxoguanosine-based agonist, a derivative thereof, and a combination thereof.

The separable linkage may be a cleavable chemical bond at a linkage site in response to a tumor microenvironment, an endosomal enzyme, a lysosomal enzyme, or pH in cells, and the active site of the toll-like receptor 7/8 agonist is exposed by cleavage of the separable linkage, thereby recovering a kinetic function of the toll-like receptor 7/8 agonist within 4 days.

The toll-like receptor 7/8 agonist may be selected from the group consisting of imiquimod, resiquimod, dactolisib, gardiquimod, sumanirole, motolimod, vesatolimod, loxoribine, SM360320, CL264, 3M-003, IMDQ, and Compound 54.

In another general aspect, the nanoparticle composition includes the toll-like receptor 7/8 agonist-cholesterol complex.

The nanoparticle may include at least one selected from the group consisting of nanoliposome, nanomicelle, solid nanoparticle, a nanoemulsion, and a polymer nanoparticle.

In still another general aspect, the adjuvant composition includes the toll-like receptor 7/8 agonist-cholesterol complex.

In still another general aspect, the vaccine composition includes the adjuvant composition and an antigen.

The antigen may be selected from the group consisting of a protein, a recombinant protein, a glycoprotein, a gene, a peptide, a polysaccharide, a lipopolysaccharide, a polynucleotide, cells, a cell lysate, bacteria, and a virus.

In still another general aspect, the composition for controlling an immune function includes the toll-like receptor 7/8 agonist-cholesterol complex as an active ingredient.

The composition for controlling an immune function may induce an activation of immune cells in a tumor microenvironment, or control functions of immunosuppressive cells.

The composition for controlling an immune function may activate at least one immune cell selected from the group consisting of an antigen-presenting cell (dendritic cell, macrophage, etc.), a natural killer cell (NK cell) and a T cell.

The composition for controlling an immune function may regulate a function of at least one immune cell selected from the group consisting of a regulatory T cell (Treg), a myeloid-derived suppressor cell (MDSC), and M2 macrophage, thereby regulating an immune function in a body.

In still another general aspect, the pharmaceutical composition for preventing or treating a cancer includes the toll-like receptor 7/8 agonist-cholesterol complex as an active ingredient.

The pharmaceutical composition may further include a chemotherapeutic agent, an immune checkpoint inhibitor, or a combination thereof.

The pharmaceutical composition may inhibit cancer proliferation, metastasis and recurrence of a cancer, or resistance to an anti-cancer therapy.

The cancer may be selected from the group consisting of breast cancer, colorectal cancer, rectal cancer, lung cancer, colon cancer, thyroid cancer, oral cancer, pharyngeal cancer, laryngeal cancer, cervical cancer, brain cancer, ovarian cancer, bladder cancer, kidney cancer, liver cancer, pancreatic cancer, prostate cancer, skin cancer, tongue cancer, uterine cancer, stomach cancer, bone cancer, and blood cancer.

In still another general aspect, the method of preventing or treating cancer includes administering a composition including the toll-like receptor 7/8 agonist-cholesterol complex as an active ingredient into a subject.

In still another general aspect, the method of preventing or treating an infectious disease includes administering a composition including the toll-like receptor 7/8 agonist-cholesterol complex as an active ingredient into a subject.

In still another general aspect, the method of preparing the toll-like receptor 7/8 agonist-cholesterol complex includes chemically bonding the cholesterol to the active site of the toll-like receptor 7/8 agonist using a cleavable linker.

The method may include mixing and reacting the toll-like receptor 7/8 agonist, a cholesteryl chloroformate, and a pyridine in a dichloromethane.

The method may include: preparing a disulfide cross-linker by dissolving 2-hydroxyethyl disulfide in a tetrahydrofuran to prepare a solution, adding and dissolving the solution in a toluene solution, and adding and dissolving N-hydrosuccinimide and triethylamine in the toluene solution; preparing a disulfide-cholesterol cross-linker by mixing and reacting the disulfide cross-linker and a cholesterol; and mixing and reacting the disulfide-cholesterol cross-linker and a toll-like receptor 7/8 agonist.

The disulfide cross-linker and the cholesterol may be mixed in a weight ratio of 3:1 to 1:1.

The disulfide-cholesterol cross-linker and the toll-like receptor 7/8 agonist may be mixed in a weight ratio of 4:1 to 1:1.

BRIEF DESCRIPTION OF THE DRAWINGS

FIG. 24 shows the result of confirming the effect of co-administration with the nanoliposome including the toll-like receptor 7/8 agonist-cholesterol complex according to one embodiment of the present disclosure and a chemotherapeutic agent.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
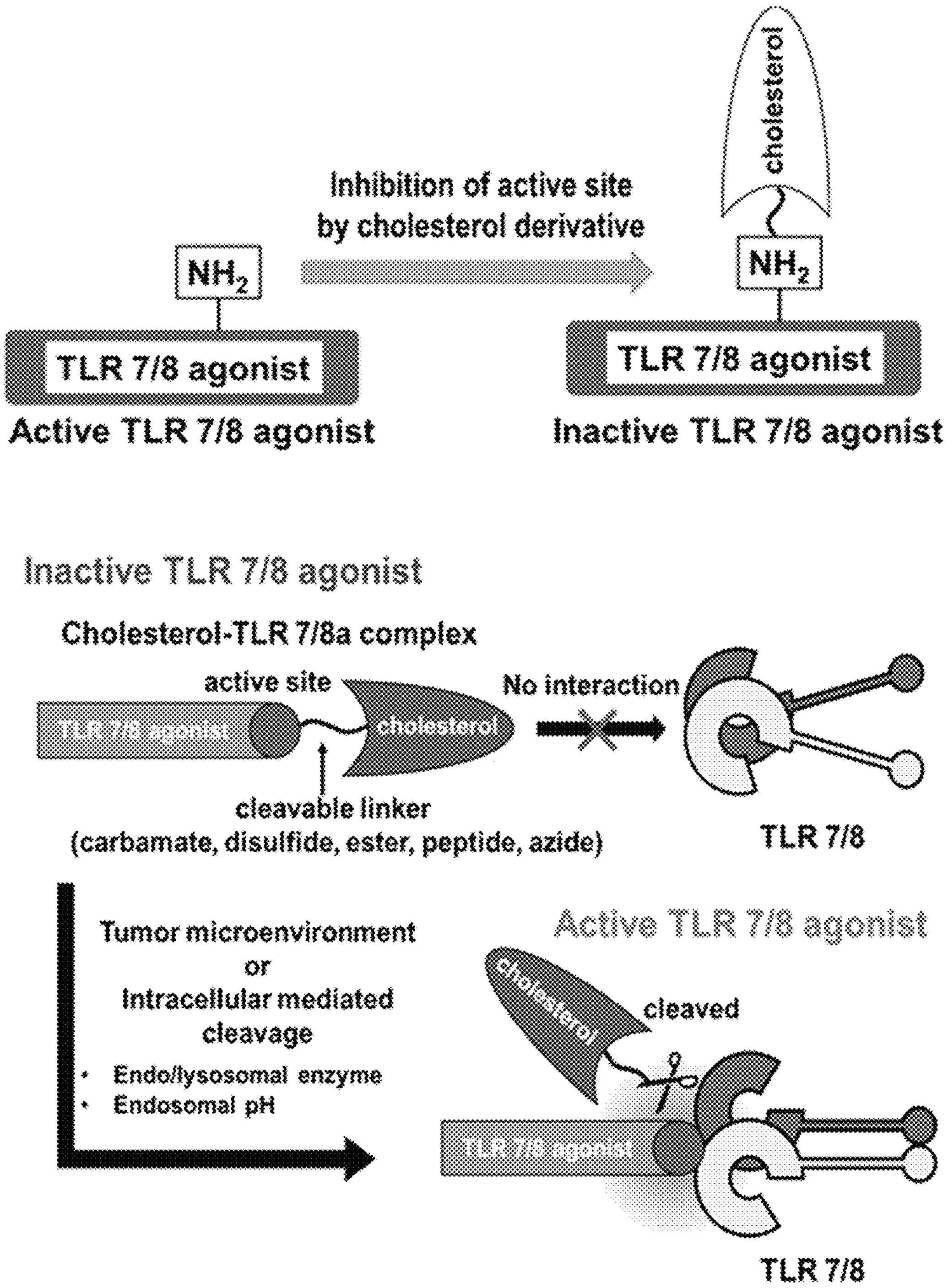
FIG. 1 is a diagram illustrating the structure and activation/inactivation mechanism of the toll-like receptor 7/8 agonist-cholesterol complex.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of this disclosure. For example, the sequences of operations described herein are merely examples, and are not limited to those set forth herein, but may be changed as will be apparent after an understanding of this disclosure, with the exception of operations necessarily occurring in a certain order. Also, descriptions of features that are known in the art may be omitted for increased clarity and conciseness.

The features described herein may be embodied in different forms and are not to be construed as being limited to the examples described herein. Rather, the examples described herein have been provided merely to illustrate some of the many possible ways of implementing the methods, apparatuses, and/or systems described herein that will be apparent after an understanding of this disclosure.

Hereinafter, while embodiments of the present disclosure will be described in detail with reference to the accompanying drawings, it is noted that examples are not limited to the same.

Throughout the drawings and the detailed description, the same reference numerals refer to the same elements. The drawings may not be to scale, and the relative size, proportions, and depiction of elements in the drawings may be exaggerated for clarity, illustration, and convenience.

Throughout the present disclosure, the phrase "combination(s) thereof" included in a Markush-type expression denotes one or more mixtures or combinations selected from the group consisting of components stated in the Markush-type expression, that is, denotes that one or more components selected from the group consisting of the components are included.

Throughout the present disclosure, the phrase that a certain element "comprises" or "includes" another element means that the certain element may further include one or more other elements but does not preclude the presence or addition of one or more other elements, unless stated to the contrary.

Throughout the present disclosure, terms such as "first," "second," "A," or "B" are used to distinguish the same terms from each other. The singular forms "a," "an," and "the" include the plural form unless the context clearly dictates otherwise.

In the present disclosure, the term "X-based" may mean that a compound includes a compound corresponding to X, or a derivative of X.

Hereinafter, the present disclosure will be described in further detail.

To solve the conventional technical problems, the present disclosure provides a toll-like receptor 7/8 agonist-cholesterol complex, which is designed to temporarily inhibit an immune activation function and recover immune activity in a tumor microenvironment or target cells, and a use thereof.

The present disclosure relates to technology in which a toll-like receptor 7/8 agonist can be applied to various pharmaceutical formulations to be effectively used in actual clinical practice, and minimize the induction of a non-specific immune response and a cytokine storm in the body.

The present disclosure relates to the design of the structure of a toll-like receptor 7/8 agonist with kinetically controlled activity, which has an inhibited immune activation function, and then recovers activity in a tumor microenvironment and target immune cells, thereby showing immune activation efficacy.

In addition, the present disclosure relates to a nanoliposome, nanoemulsion, nanomicelle and a polymer nanoparticle, which include a toll-like receptor 7/8 agonist-cholesterol complex. The term "including" may mean a form contained within regardless of a chemical bond, a form of being attached to the surface of nanoparticle, or a form of being sandwiched between a nanoparticle structure, but any form including the complex of the present disclosure is used without limitation.

In addition, the present disclosure relates to an adjuvant composition, which includes a cholesterol-toll-like receptor 7/8 agonist complex.

In addition, the present disclosure relates to a vaccine composition, which includes an adjuvant composition including a cholesterol-toll-like receptor 7/8 agonist complex and an antigen.

In addition, the present disclosure relates to an immune cell activating composition, which includes a cholesterol-toll-like receptor 7/8 agonist complex.

In addition, the present disclosure relates to an immunosuppressive cell function-controlling composition, which includes a cholesterol-toll-like receptor 7/8 agonist complex.

In addition, the present disclosure relates to a cancer immunotherapeutic composition, which includes a cholesterol-toll-like receptor 7/8 agonist complex.

In addition, the present disclosure relates to an anticancer composition, which includes a cholesterol-toll-like receptor 7/8 agonist complex; and further includes an anticancer agent and an immune checkpoint inhibitor.

However, technical problems to be solved in the present disclosure are not limited to the above-described problems, and other problems which are not described herein will be fully understood by those of ordinary skill in the art from the following descriptions.

The toll-like receptor 7/8 agonist to which cholesterol is chemically linked according to the present disclosure (cholesterol-toll-like receptor 7/8 agonist complex) cannot only prevent penetration into blood due to increased lipophilicity, but also remarkably reduce side effects and cytotoxicity of a conventional toll-like receptor 7/8 agonist, since its immune activation function is inhibited in an environment other than a tumor microenvironment or endosomes in immune cells.

In addition, after delivery to a tumor microenvironment and immune cells, the cholesterol and the toll-like receptor 7/8 agonist are slowly separated and consistently react with the toll-like receptor for a long time by kinetic immune modulation of the active site of the toll-like receptor 7/8 agonist, so that it can remarkably increase a therapeutic effect by increasing persistence of immune activation of immune cells compared to when the toll-like receptor agonist is used alone.

In addition, since the cholesterol-toll-like receptor 7/8 agonist complex can induce immune activation of antigen-presenting cells (dendritic cells, macrophages, etc.), natural killer cells (NK cells) or T cells, and regulate the function of immune cells exhibiting an immunosuppressive action (regulatory T cells (Tregs), myeloid derived suppressor cells (MDSCs) or M2 macrophages) in a tumor microenvironment, it can not only exhibit an anticancer effect, but also remarkably increase an anticancer effect due to a synergistic effect by co-administration with an immune checkpoint inhibitor or a chemotherapeutic agent.

Moreover, since the cholesterol-toll-like receptor 7/8 agonist complex is based on cholesterol, which is a basic component of a biomembrane, it can be easily prepared in various forms such as a nanoemulsion, a nanoliposome and a nanomicelle in combination with various lipids, and therefore, intracellular delivery efficacy can increase. For this reason, in the present disclosure, the cholesterol-toll-like receptor 7/8 agonist complex can be prepared in various forms, and is also expected to remarkably increase the therapeutic effect on various diseases by inducing immune activation by being included in various pharmaceutical compositions.

In the present disclosure, in the toll-like receptor 7/8 agonist-cholesterol complex, a cholesterol group is linked to an active site of a toll-like receptor 7/8 agonist in a cleavable form, and thus an immune activation function is temporarily inhibited (FIG. 1). The inhibition may mean that a function of the active site of the toll-like receptor 7/8 agonist is retarded.

In the present disclosure, the complex is crosslinked to a site at which cleavage is induced due to a tumor microenvironment and/or intracellular environment, particularly, physiological environments (low pH, enzyme, glutathione, etc.) of an endosome and a lysosome (FIG. 1). Specifically, under a tumor microenvironment, there may be a linkage form that can be regulated so that cleavage occurs by a specific stimulus such as a pH, a temperature, redox potential, ultrasound, an enzyme, a magnetic field or near-infrared light. While the linkage is preferably formed by a carbamate, disulfide, ester, peptide or azide bond, any bond in a cleavable form may be used without limitation.

In addition, in the present disclosure, in the complex, cholesterol and a toll-like receptor 7/8 agonist may be separated due to various enzymes present in a tumor microenvironment and cells, such as acid phosphatase, acid phyrophosphatase, phosphodiesterase, phosphoprotein phosphatase, phosphatidic acid phosphatase, arylsulfatase, proteases, cathepsins, collagenase, arylamidase, peptidase, acid ribonuclease, acid deoxyribonuclease, lipases, triglyceride lipase, phospholipase, esterase, carboxyesterase, glucocerebrosidase, galactocerebrosidase, sphingomyelinase, glycosidases, alpha-glucosidase, beta-glucosidase, beta-galactosidase, alpha-mannosidase, alpha-ucosidase, beta-xylosidase, alpha-N-acetylhexosaminidase, beta-N-acetylhexosaminidase, sialidase, lysozyme, hyaluronidase, and beta-glucuronidase.

In the present disclosure, as the toll-like receptor 7/8 agonist is prepared by chemically linking cholesterol such that it is not absorbed into blood vessels in the body, the disadvantages of a salt-form toll-like receptor 7/8 agonist are overcome.

In the present disclosure, the complex is easily prepared in various forms such as a nanoliposome, a nanomicelle, and a nanoemulsion by easy interaction with various materials such as various lipid materials and saponins, thereby increasing delivery efficiency into immune cells.

The "cholesterol" used herein is a type of lipid, and encompasses steroid-based organic materials having a hydrophobic property, and the cholesterol may include various derivatives based on a cholesterol structure, and compounds that can be obtained by chemically changing a part of cholesterol. Preferably, the cholesterol includes bile acids (cholic acid, deoxycholic acid, lithocholic acid, and chenodeoxycholic acid), vitamin D, and steroid hormones (testosterone, estradiol, cortisol, aldosterone, prednisolone, and prednisone), but the present disclosure is not limited thereto. In addition, the cholesterol is a material that assists the toll-like receptor 7/8 agonist to be located on the surface and in various forms of nanoparticles, and may be replaced with lipid materials having a similar function thereto, for example, natural lipids such as a phospholipid, and synthetic lipids.

The "toll-like receptor 7/8 agonist-based material" used herein may be selected from the group consisting of toll-like receptor 7 or 8 agonists, such as an imidazoquinoline-based compound, an 8-hydroxyadenine-based compound, a pteridone-based compound, a 2-aminopyrimidine-based compound, a benzoazepine-based compound, and a 7-thia-8-oxoguanosine-based compound. Here, the imidazoquinoline-based compound includes compounds disclosed in WO 2018 196823, WO 2011 049677, WO 2011 027022, WO 2017 102652, and WO 2019 040491, or pharmaceutically acceptable salts thereof, but the present disclosure is not limited thereto. In addition, the 8-hydroxyadenine-based compound includes compounds disclosed in WO 2012 080730, WO 2013 068438, WO 2019 036023, WO 2019 035969, WO 2019 035970, WO 2019 035971, WO 2019 035968, CN 108948016, US 2014 8846697, WO 2016 023511, WO 2017 133683, WO 2017 133686, WO 2017 133684, WO 2017 133687, WO 2017 076346, WO 2018 210298, WO 2018 095426, WO 2018 068593, WO 2018 078149, WO 2018 041763, or pharmaceutically acceptable salts thereof, but the present disclosure is not limited thereto. The pteridone-based compound includes compounds disclosed in US 2010 0143301, WO 2016 007765, WO 2016 044182, WO 2017 035230, WO 2017 219931, WO 2011 057148, and CN 1087 94486, or pharmaceutically acceptable salts thereof, but the present disclosure is not limited thereto. The 2-aminopyrimidine-based compound includes compounds disclosed in WO 2010 133885, WO 2012066335, WO 2012 066336, WO 2012 067268, WO 2013 172479, WO 2012 136834, WO 2014 053516, WO 2014 053595, US 2018 0215720, WO 2012 156498, WO 2014 076221, WO 2016 141092, WO 2018 045144, WO 2015 014815, WO 2018 233648, WO 2014 207082, WO 2014 056593, WO 2018 002319, and WO 2013 117615, or pharmaceutically acceptable salts thereof, but the present disclosure is not limited thereto. The benzoazepine-based compound includes compounds disclosed in WO 2007 024612, WO 2010 014913, WO 2010 054215, WO 2011 022508, WO 2011 022509, WO 2012 097177, WO 2012 097173, WO 2016 096778, WO 2016 142250, WO 2017 202704, WO 2017 202703, WO 2017 216054, WO 2017 046112, and WO 2017 197624, or pharmaceutically acceptable salts thereof, but the present disclosure is not limited thereto. The 7-thia-8-oxoguanosine-based compound includes compounds disclosed in WO 2016 180691, WO 2016 055553, WO 2016 180743, and WO 2016 091698, or pharmaceutically acceptable salts thereof, but the present disclosure is not limited thereto. In addition, toll-like receptor 7/8 compounds disclosed in PCT/US2009/035563, PCT/US2015/028264, PCT/US2016/020499, WO 2015 023598 and PCT/US 2015/039776, or pharmaceutically acceptable salts thereof may be included, but the present disclosure is not limited thereto. All available toll-like receptor 7/8 agonists that can be easily inferred by those of skill in the art are included.

The "toll-like receptor 7/8 agonist" used herein may be applied to a "toll-like receptor 3 agonist" or "toll-like receptor 9 agonist," which is delivered into cells and has a receptor in an endosome, in the same way, and thus the "toll-like receptor 3 agonist" or "toll-like receptor 9 agonist" may also form a complex with cholesterol, but the present disclosure is not limited thereto.

Throughout the disclosure, the toll-like receptor 7/8 agonist-cholesterol complex may regulate an immune function of immune cells such that the immune activation of antigen-presenting cells (dendritic cells, macrophages, etc.), natural killer cells or T cells is induced, or regulate an immune function of immune cells by regulating the function of immune cells (regulatory T cells (Tregs), myeloid derived suppressor cells (MDSCs) and M2 macrophages), which exhibit an immunosuppressive action, in a tumor microenvironment. The function of the immune cells exhibiting an immunosuppressive action may be regulated by inhibiting the action of Tregs or MDSCs, or reducing the cell count, or regulated by a method of converting MDSCs into antigen-presenting cells inducing an anticancer immune function. Alternatively, M2 macrophages may be converted into M1 macrophages.

The "co-administration" or "combinational administration" used herein is administration of a toll-like receptor 7/8 agonist-cholesterol complex, along with various materials such as an antigen, an immune checkpoint inhibitor, an adjuvant, an immune activation material, and a chemotherapeutic agent, and there are no limitations to the type and shape of the materials.

The "chemotherapeutic agent" used herein may be any compound known to the art, which can be used in cancer treatment, without limitation, and the chemotherapeutic agent may be paclitaxel, docetaxel, 5-flurouracil, alendronate, doxorubicin, simvastatin, hydrazinocurcumin, amphotericin B, ciprofloxacin, rifabutin, rifampicin, efavirenz, cisplatin, theophyline, pseudomonas exotoxin A, zoledronic acid, trabectedin, siltuximab, dasatinib, sunitinib, apatinib, 5,6-dimethylxanthenone-4-acetic acid, silibinin, PF-04136309, trabectedin, carlumab, BLZ945, PLX3397, emactuzumab, AMG-820, IMC-CS4, GW3580, PLX6134, N-acetyl-I-cysteine, vitamin C, bortezomib, aspirin, salicylates, indolecarboxamide derivatives, quinazoline analogues, thalidomide, prostaglandin metabolites, 2ME2, 17-AAG, camptothecin, topotecan, pleurotin, 1-methylpropyl, 2-imidazolyl disulfide, tadalafil, sildenafil, L-AME, nitroaspirin, celecoxib, NOHA, bardoxolone methyl, D,L-1-methyl-tryptophan, gemcitabine, axitinib, sorafenib, cucurbitacin B, JSI-124, anti-IL-17 antibodies, anti-glycan antibodies, anti-VEGF antibodies, bevacizumab, anthracycline, tasquinimod, imatinib or cyclophosphamide, but the present disclosure is not limited thereto.

The "immune checkpoint inhibitor" used herein includes all methods of treating cancer, which activate the immune function of immune cells to fight cancer cells, and the immune checkpoint inhibitor includes, for example, anti-PD-1, anti-PD-L1, anti-CTLA-4, anti-KIR, anti-LAG3, anti-CD137, anti-OX40, anti-CD276, anti-CD27, anti-GITR, anti-TIM3, anti-41BB, anti-CD226, anti-CD40, anti-CD70, anti-ICOS, anti-CD40L, anti-BTLA, anti-TCR or anti-TIGIT, but the present disclosure is not limited thereto.

The immune activation material used herein includes all materials for activating immune cells, and the immune activation material is, for example, a toll-like receptor agonist, a saponin, an antiviral peptide, an inflammasome inducer, a NOD ligand, a cytosolic DNA sensor (CDS) ligand, a stimulator of interferon gene (STING) ligand, an emulsion or alum, but the present disclosure is not limited thereto.

The "antigen" used herein includes all materials causing an immune response in a body, and is preferably a pathogen (bacteria, a virus, et. al.), a chemical compound, pollen, cancer cells, shrimp, or a peptide or protein derived from the antigen, and more preferably, a cancer antigen peptide or a material that can cause an immune response in a body, but the present disclosure is not limited thereto. The antigen is preferably a protein, a recombinant protein, a glycoprotein, a gene, a peptide, a polysaccharide, a lipopolysaccharide, a polynucleotide, a cell, a cell lysate, a bacterium or a virus, and more preferably, a cancer antigen peptide. The glycoprotein may be an antibody, an antibody fragment, a structural protein, a regulatory protein, a transcription factor, a toxin protein, a hormone, a hormone derivative, an enzyme, an enzyme fragment, a transport protein, a receptor, a receptor fragment, a biodefense inducer, a storage protein, a movement protein, an exploitive protein, or a reporter protein. However, if it is a material that can induce an immune response by acting as an antigen in a body, it is not limited thereto.

The "vaccine" used herein refers to a biological preparation containing an antigen provoking an immune response in a body, and an immunogen which creates immunity in a body by injection or oral administration to a human or animal for the prevention of infection. The animal is a human or a non-human animal such as a pig, a cow, a horse, a dog, a goat, or a sheep, but the present disclosure is not limited thereto.

The "prevention" used herein refers to all actions of inhibiting a disease such as cancer, an immune disease or an infectious disease or delaying the onset thereof by administration of the composition according to the present disclosure.

The "treatment" used herein refers to all actions involved in alleviating or beneficially changing symptoms of a disease such as cancer, an immune disease or an infectious disease by administration of the composition according to the present disclosure.

The "individual or subject" used herein refers to a target to which the composition of the present disclosure may be administered, and there is no limitation to the subject.

The "cancer" used herein refers to the generic term for various types of blood cancer and malignant solid tumors, which can expand locally by infiltration and systemically through metastasis. Although not particularly limited thereto, specific examples of cancer include colorectal cancer, adrenal cancer, bone cancer, brain cancer, breast cancer, bronchial cancer, colon cancer and/or rectal cancer, gallbladder cancer, gastrointestinal cancer, head and neck cancer, kidney cancer, laryngeal cancer, liver cancer, lung cancer, neural tissue cancer, pancreatic cancer, prostate cancer, parathyroid cancer, skin cancer, stomach cancer and thyroid cancer.

Other examples of cancer include adenocarcinoma, adenoma, basal cell carcinoma, cervical dysplasia and carcinoma in situ, Ewing's sarcoma, squamous cell carcinoma, ductal carcinoma, malignant brain tumor, hairy-cell tumor, intestinal ganglioneuroma, hyperplastic corneal nerve tumor, islet cell carcinoma, Kaposi's sarcoma, leiomyoma, leukemia, lymphoma, malignant carcinoid, malignant melanoma, malignant hypercalcemia, marfanoid habitus tumor, medullary carcinoma, metastatic skin cancer, mucosal neuroma, myelodysplastic syndrome, myeloma, mycosis fungoides, neuroblastoma, osteosarcoma, osteogenic and other sarcomas, ovarian cancer, pheochromocytoma, polycythemia, primary brain tumor, small-cell lung cancer, ulcerative and papillary squamous cell carcinoma, seminoma, soft tissue sarcoma, retinoblastoma, rhabdomyosarcoma, renal cell tumor or renal cell carcinoma (RCC), reticulum cell sarcoma, and Wilms' tumor. Examples of cancer also include astrocytoma, gastrointestinal stromal tumor (GIST), glioma or glioblastoma, hepatocellular carcinoma (HCC), and pancreatic neuroendocrine cancer.

The term "infectious disease" includes all diseases induced by infection caused by heterogenous organisms such as bacteria and viruses.

The "pharmaceutical composition" or "vaccine composition" used herein is prepared in the form of a capsule, tablet, granule, injection, ointment, powder or beverage, and the pharmaceutical composition or vaccine composition may be targeted at a human. The pharmaceutical composition or vaccine composition may be used in an oral formulation such as a powder, granule, capsule, tablet or an aqueous suspension, externals, a suppository, and a sterile injectable solution according to a conventional method, but the present disclosure is not limited thereto.

The pharmaceutical composition or vaccine composition of the present disclosure may include a pharmaceutically acceptable carder. As pharmaceutically acceptable carriers, a binder, a lubricant, a disintegrant, an excipient, a solubilizer, a dispersant, a stabilizer, a suspending agent, a color and a flavor may be used for oral administration, a mixture of a buffer, a preservative, a pain relief agent, a solubilizer, an isotonic agent and a stabilizer may be used for an injectable, and a base, an excipient, a lubricant and a preservative may be used for local administration. The pharmaceutical composition or vaccine composition of the present disclosure may be prepared in various dosage forms by mixing the above-described pharmaceutically acceptable carriers. For example, for oral administration, the pharmaceutical composition or vaccine composition of the present disclosure may be prepared in various dosage forms such as a tablet, a troche, a capsule, an elixir, a suspension, a syrup and a wafer, and for injectables, the pharmaceutical composition or vaccine composition of the present disclosure may be prepared in a unit dose ampoule or multiple dose forms. In addition, the pharmaceutical composition or vaccine composition of the present disclosure maybe formulated as a solution, a suspension, a tablet, a capsule or a sustained-release preparation.

Meanwhile, examples of carriers, excipients and diluents suitable for preparation may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. The examples of carriers, excipients and diluents may also include a filler, an anti-agglomerate, a glidant, a wetting agent, a fragrance, an emulsifier, and a preservative.

Administration routes for the pharmaceutical composition or vaccine composition according to the present disclosure may include, but are not limited to, oral, intravenous, intramuscular, intraarterial, intramedullary, intrathecal, intracardiac, transdermal, subcutaneous, intraperitoneal, intranasal, intraperitoneal, intranasal, intestinal, local, sublingual or rectal administration. Oral or parenteral administration is preferable. The term "parenteral" used herein means subcutaneous, intracutaneous, intravenous, intramuscular, intraarticular, intrabursal, intrasternal, intrathecal, intralesional and intracranial injection techniques. The pharmaceutical composition or vaccine composition of the present disclosure may be administered in the form of a suppository for rectal administration.

The pharmaceutical composition or vaccine composition of the present disclosure may be changed variously according to various factors including the activity of a specific compound used, age, body weight, general health, sex, diet, administration time, administration route, excretion rate, drug formulation, and the severity of a specific disease to be prevented or treated, and a dosage of the pharmaceutical composition may be suitably selected by those of ordinary skill in the art depending on a patient's condition, body weight, the severity of a disease, a drug type, an administration route and an administration duration, and may be 0.0001 to 500 mg/kg or 0.001 to 500 mg/kg per day. The pharmaceutical composition of the present disclosure may be administered once a day or several times in divided portions. The dose does not limit the scope of the present disclosure in any way.

The pharmaceutical composition or vaccine composition according to the present disclosure may be formulated as a pill, a caplet, a capsule, a liquid, a gel, a syrup, a slurry or a suspension.

In addition, the vaccine composition according to the present disclosure may further include a conventionally known “adjuvant”. The adjuvant generally encompasses all materials increasing humoral and/or cellular immune response(s) against an antigen, and any adjuvant known in the art can be used without limitation. For example, immunity may be increased by further adding a Freund’s complete or incomplete additive to the vaccine composition according to the present disclosure. In addition, in the case of the vaccine composition, if necessary, optionally repeated antigen stimulation may be performed after an initial dose.

Hereinafter, the present disclosure will be described in further detail by specific embodiments. The below embodiments are for illustration only and the scope of the present disclosure is not limited thereto

EXAMPLES

Example 1: Synthesis of Toll-Like Receptor 7/8 Agonist-Cholesterol Complex

Various toll-like receptor 7/8 agonists (imidazoquinoline-based, 8-hydroxyadenine-based, pteridone-based, 2-amino-pyrimidine-based, benzoazepine-based, and 7-thia-8-oxoguanosine-based) conjugated to cholesterol were prepared by a chemical reaction such as Reaction Scheme 1 or 2. The toll-like receptor 7/8 agonist may be prepared by reacting an active site of the toll-like receptor 7/8 agonist, an amine group ($NH_2$), with a cholesterol derivative that can form a bond with a carbamate, a disulfide, an ester, a peptide or an azide. The derivative encompasses similar compounds obtained by chemically changing a part of a toll-like receptor 7/8 agonist.

[Reaction Scheme 1]

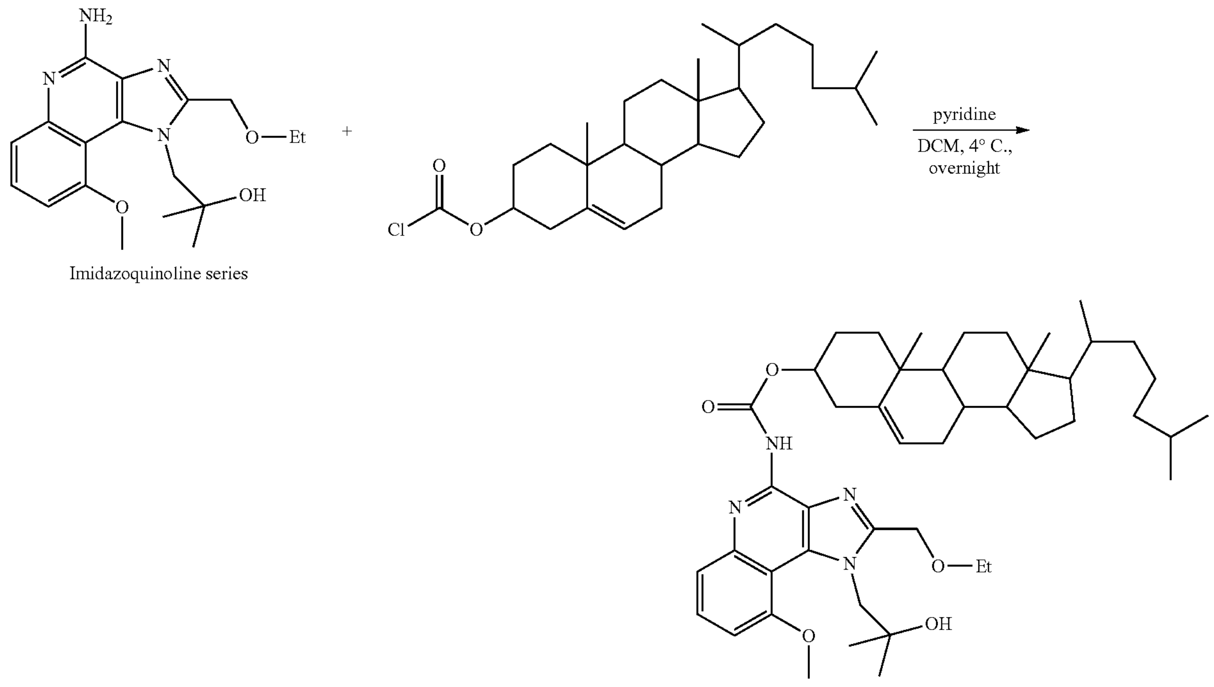

Imidazoquinoline series

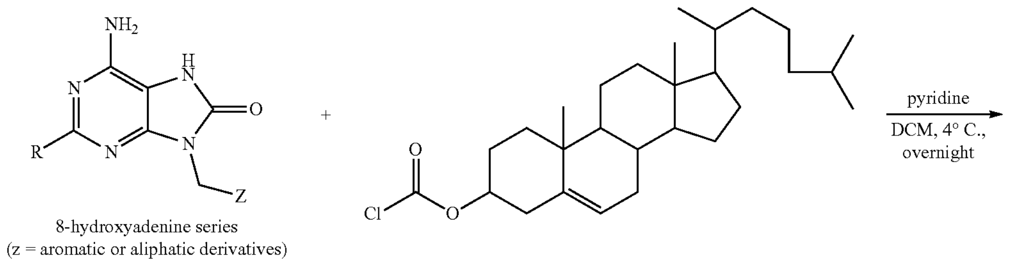

8-hydroxyadenine series
(z = aromatic or aliphatic derivatives)

-continued
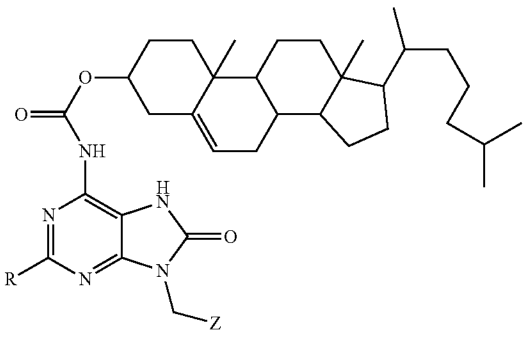
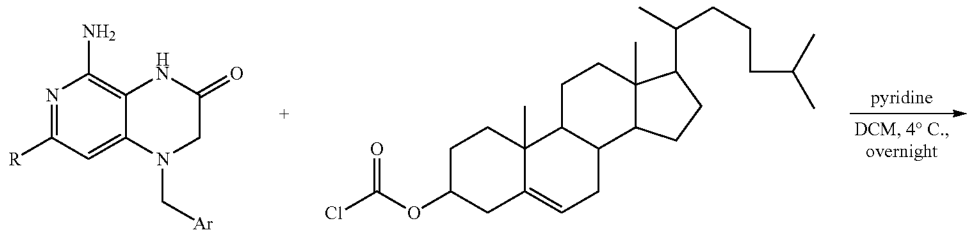
Pteridone series
(Ar = aromatic derivatives)
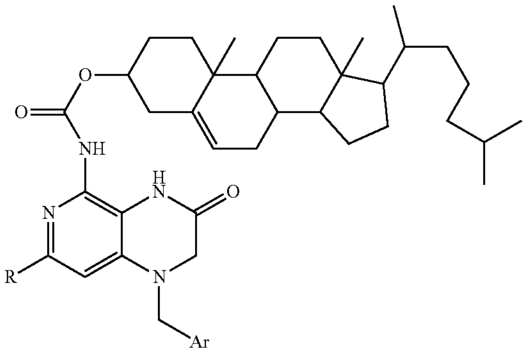
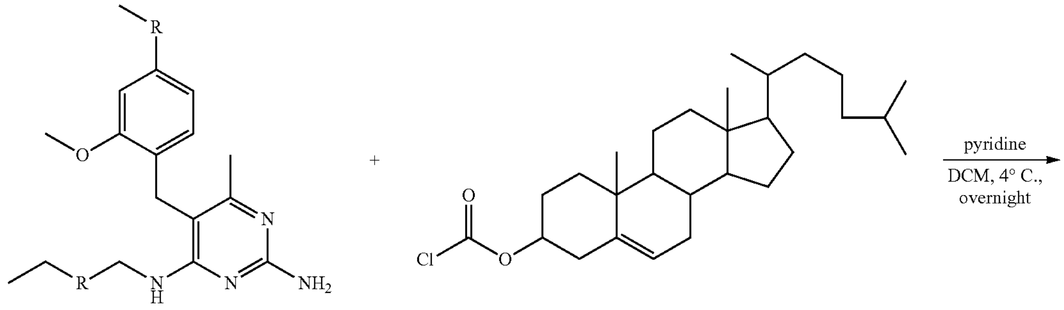
2-aminopyrimidine series
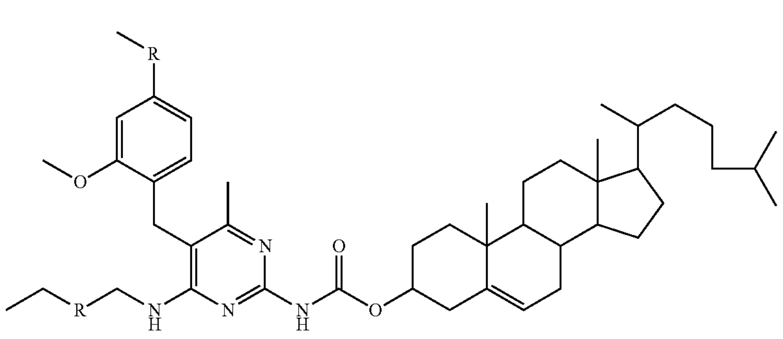

-continued
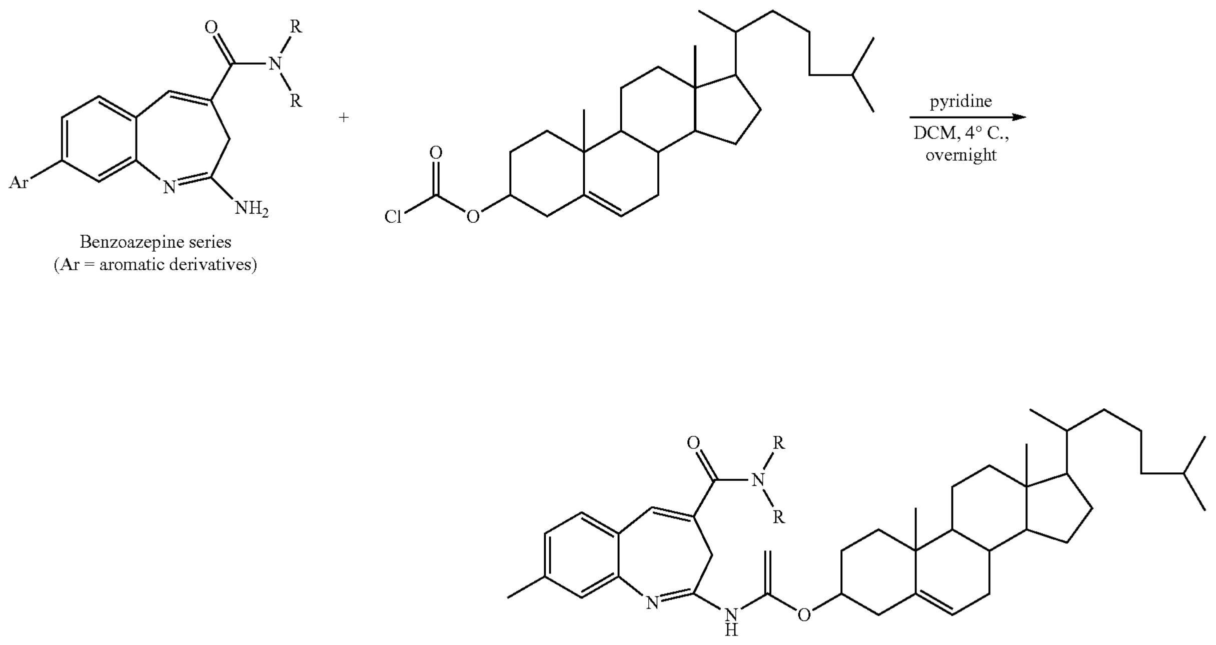
Benzoazepine series
(Ar = aromatic derivatives)
In the above reaction scheme, R is a side chain having an aliphatic or aromatic group, and may include —NH—, —CO—, —CONH—, —CSNH—, —COO—, —CSO—, —$SO_2$NH—, —$SO_2$—, —SO—, and —O—.
[Reaction Scheme 2]
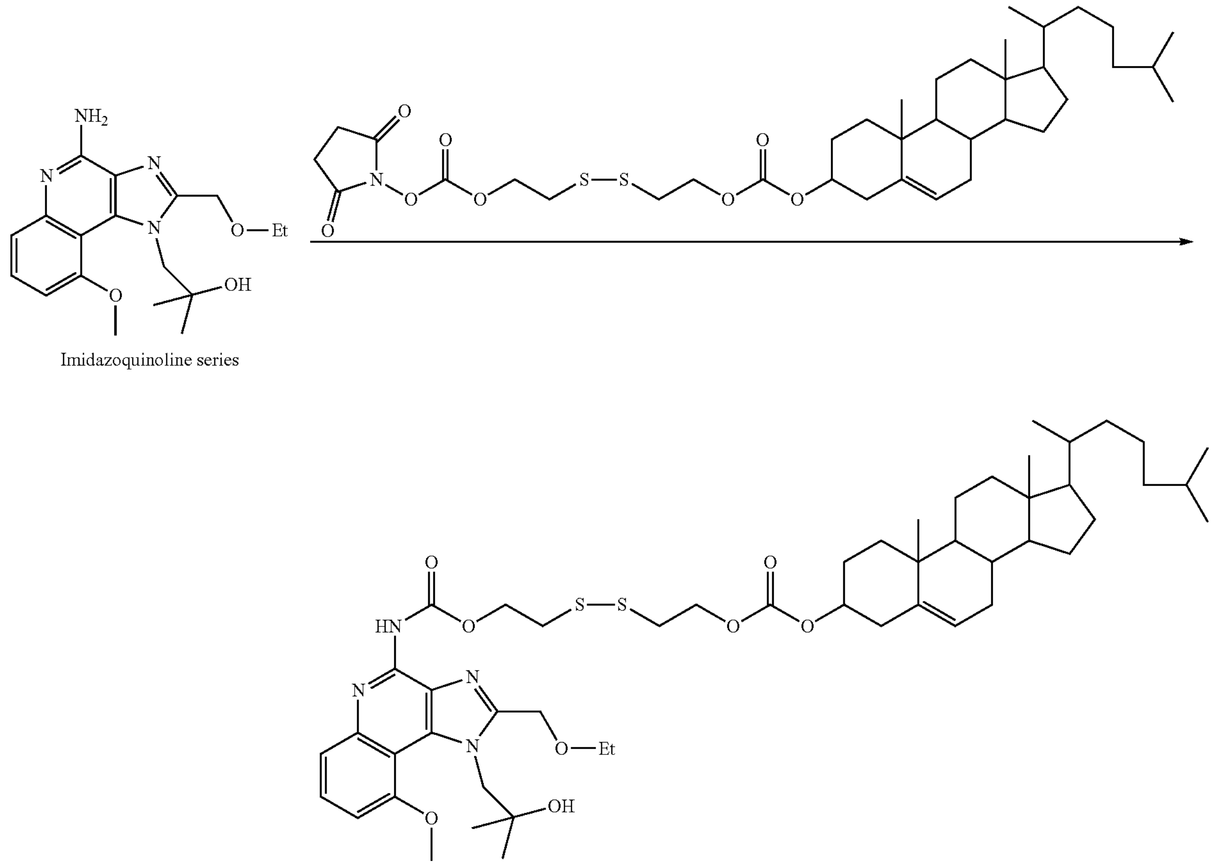
Imidazoquinoline series -continued
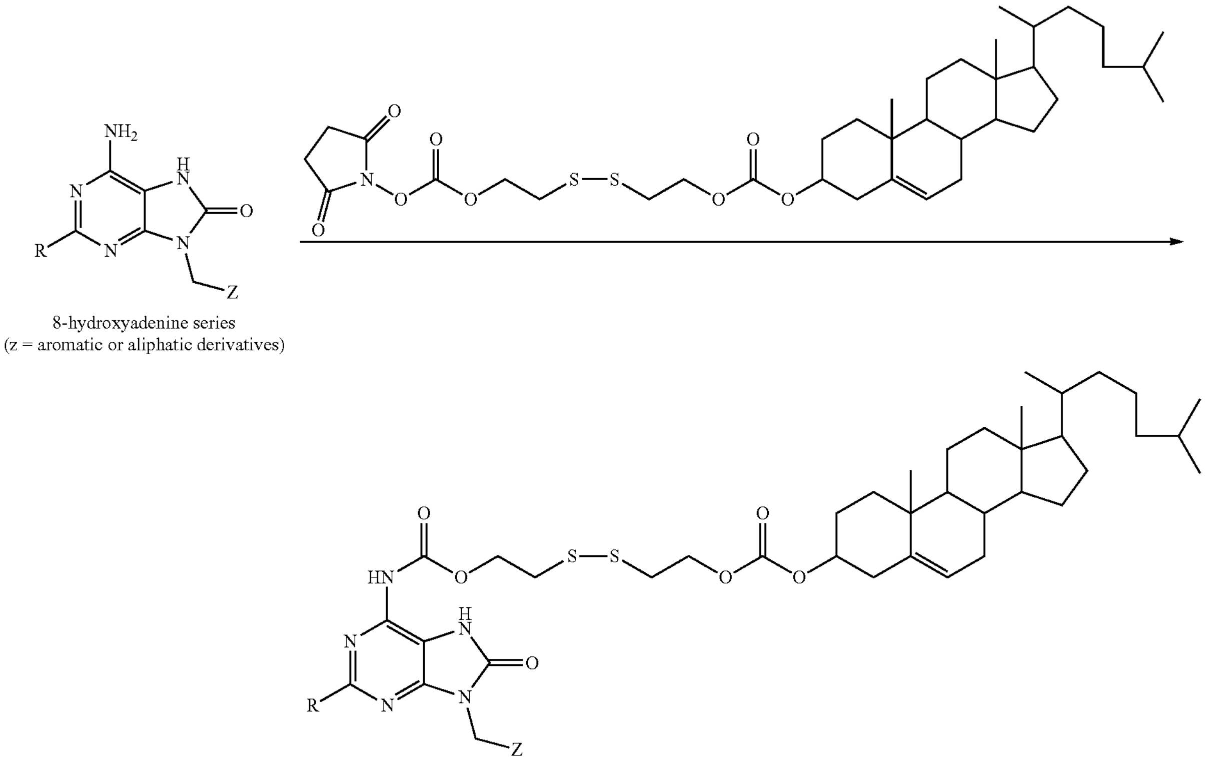
8-hydroxyadenine series
(z = aromatic or aliphatic derivatives)
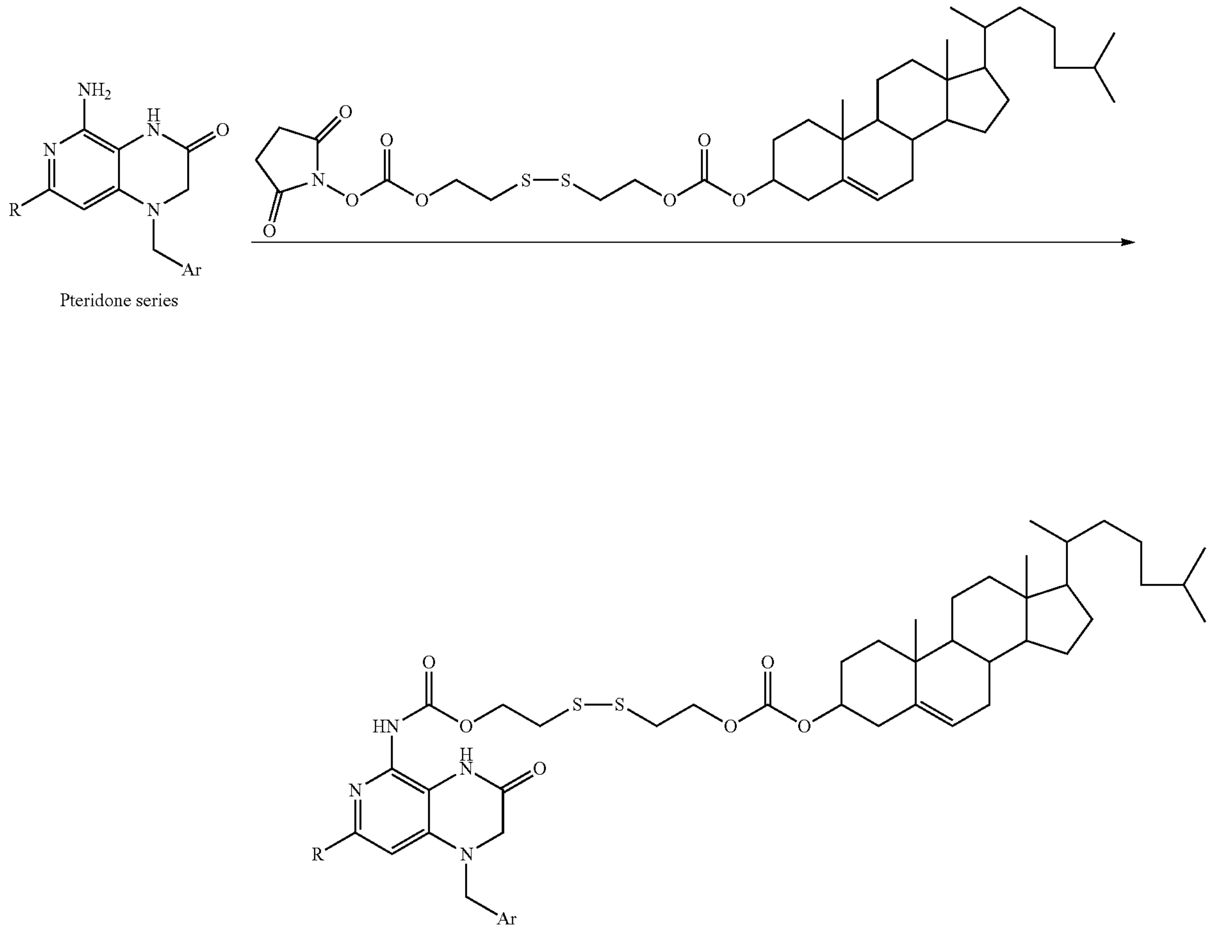
Pteridone series -continued
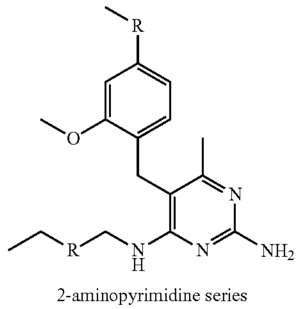
2-aminopyrimidine series
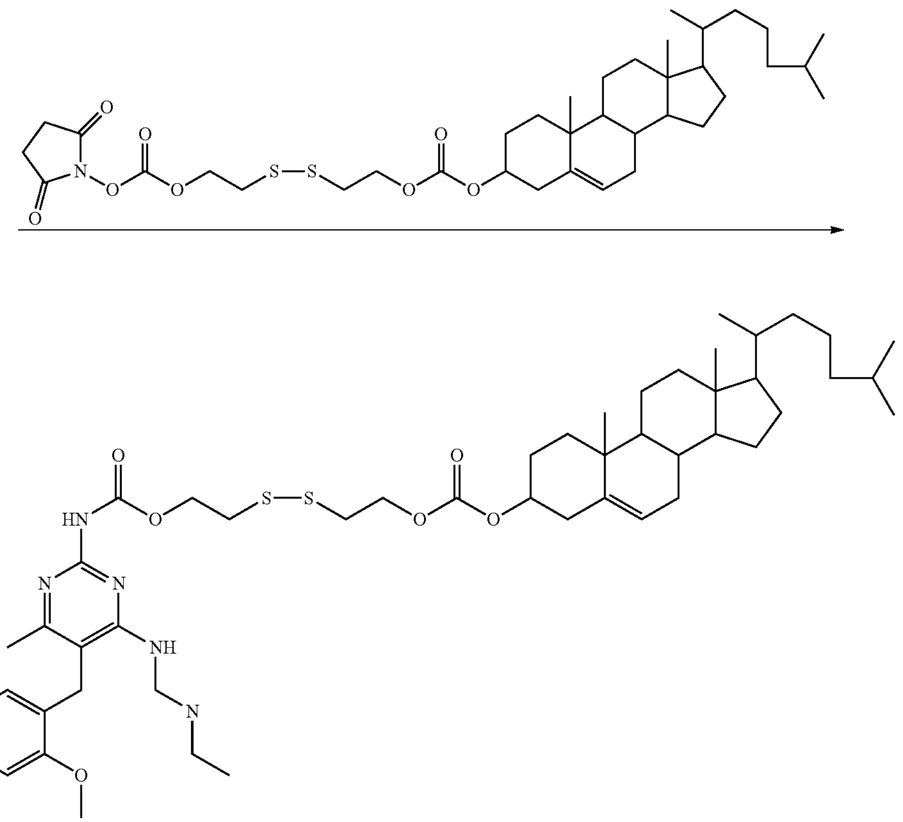
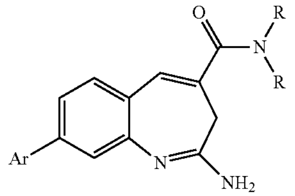
Benzoazepine series
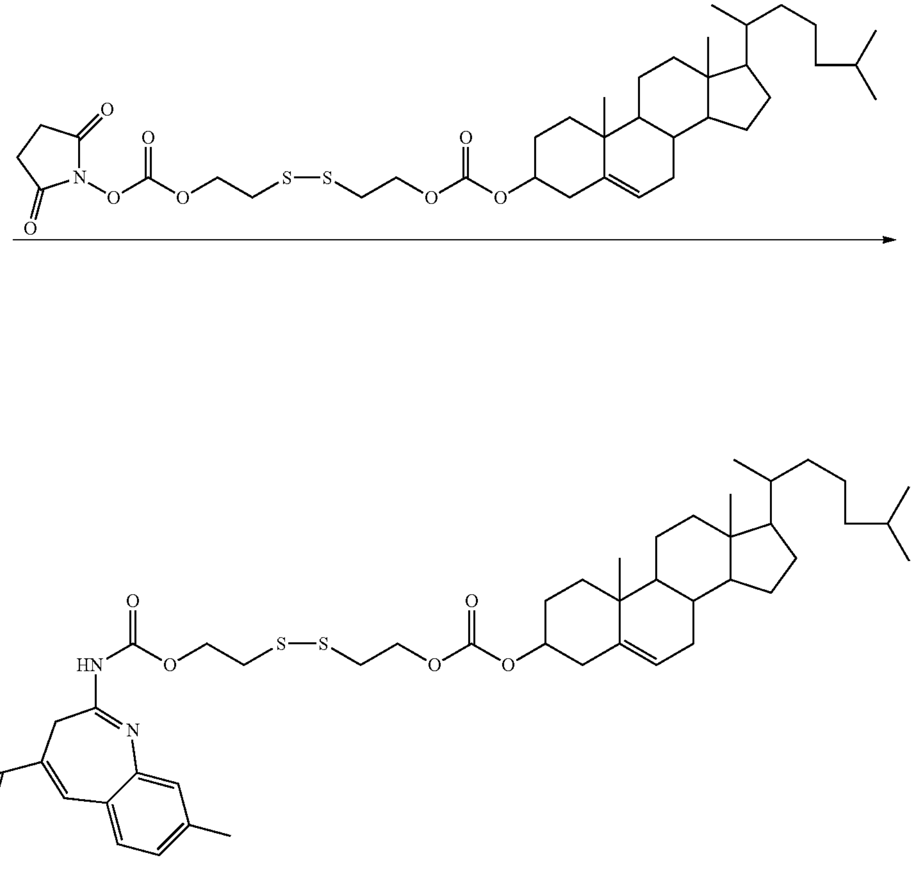

In the above reaction scheme, R is a side chain having an aliphatic or aromatic group, and may include —NH—, —CO—, —CONH—, —CSNH—, —COO—, —CSO—, —$SO_2$NH—, —$SO_2$—, —SO—, and —O—.

1.1. Synthesis of Resiquimod-Cholesterol Complex Having Carbamate Bond

Figure 2:
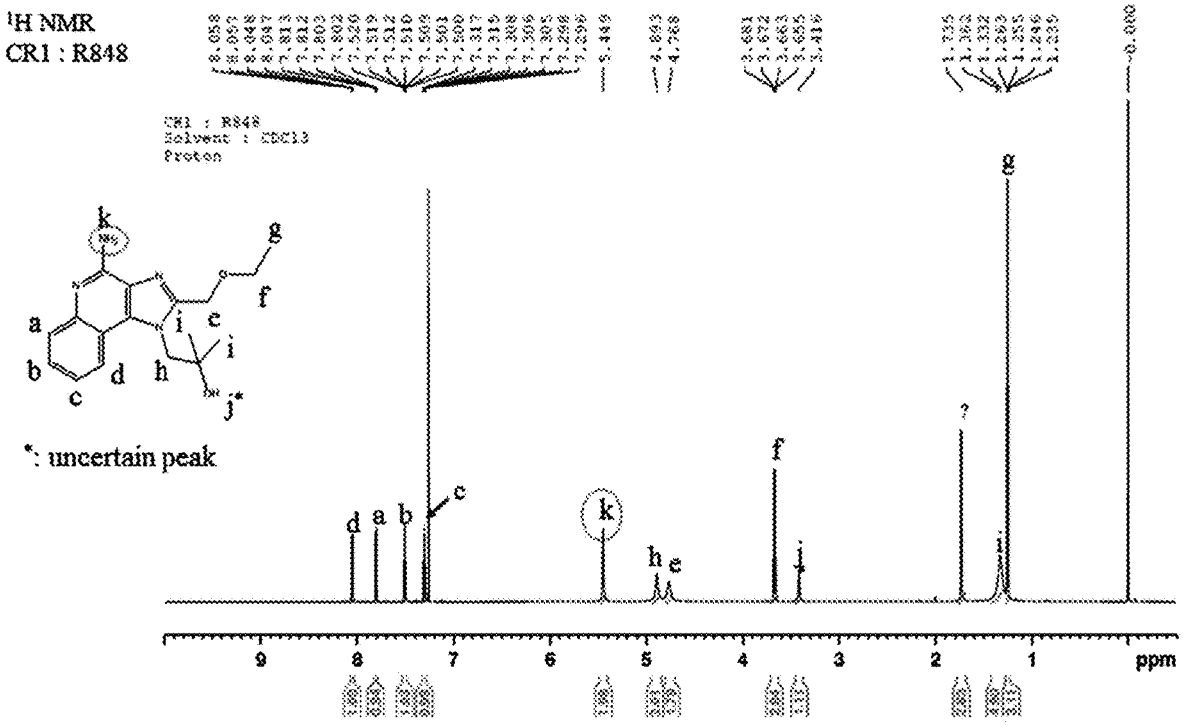
FIG. 2 shows the result of verifying the structure of the toll-like receptor 7/8 agonist according to one embodiment of the present disclosure through $^{1}$H-NMR.
Figure 3:
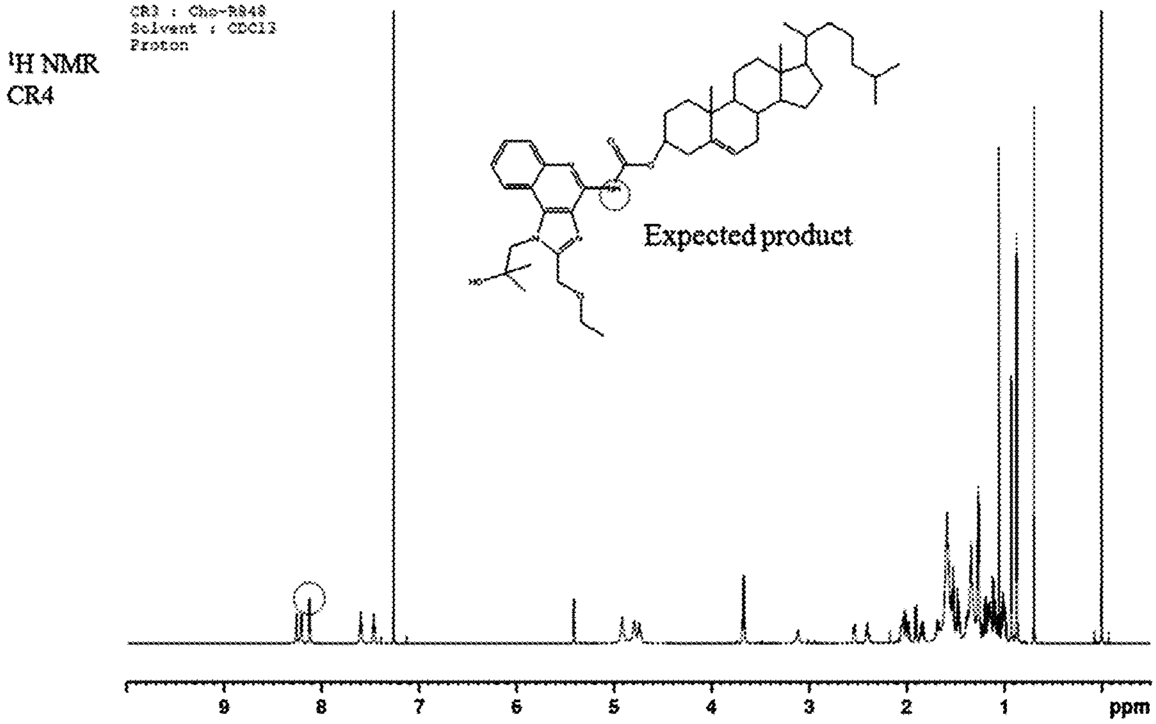
FIG. 3 shows the result of verifying the structure of the cholesterol-linked toll-like receptor 7/8 agonist according to one embodiment of the present disclosure through $^{1}$H-NMR.
Figure 4:
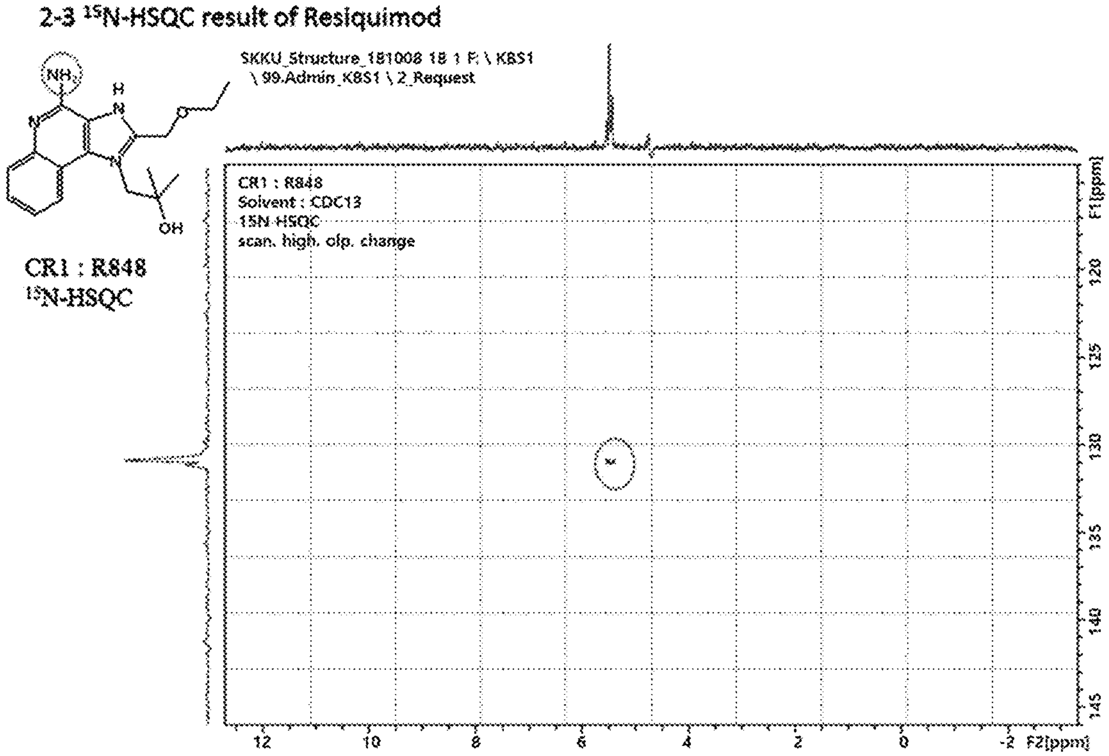
FIG. 4 shows the result of verifying the structure of the toll-like receptor 7/8 agonist according to one embodiment of the present disclosure through $^{15}$N-HSQC.
Figure 5:
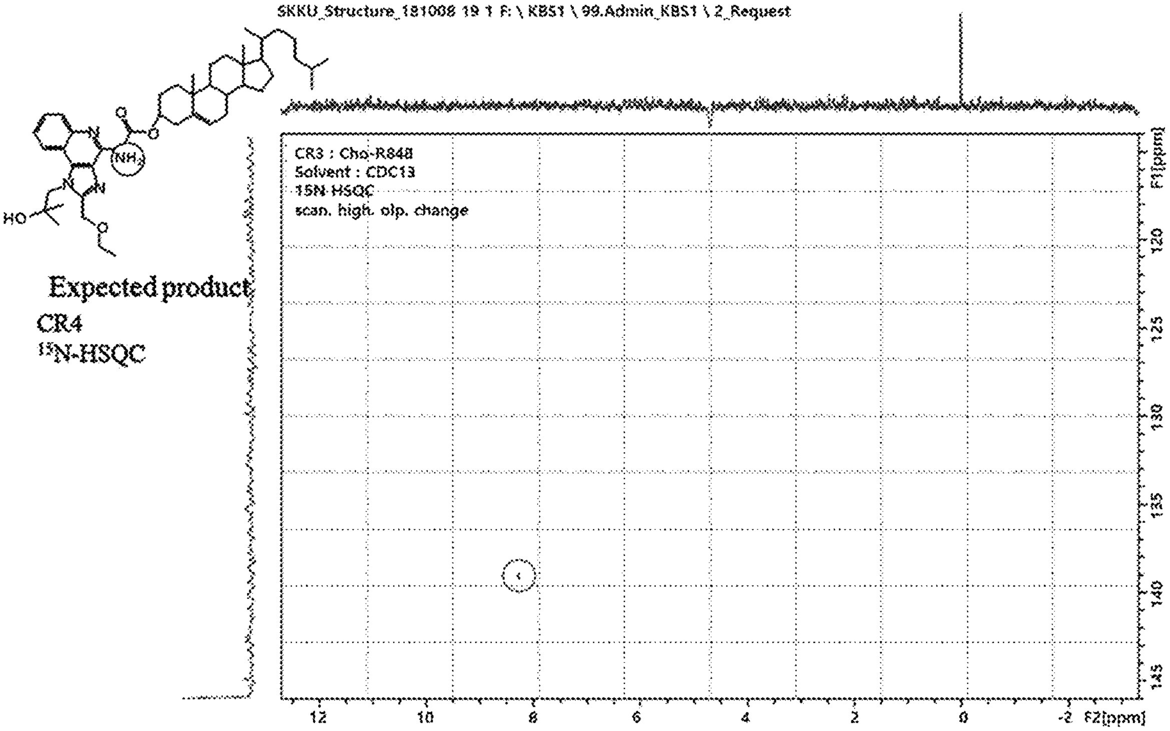
FIG. 5 shows the result of verifying the structure of the cholesterol-linked toll-like receptor 7/8 agonist according to one embodiment of the present disclosure through $^{15}$N-HSQC.
Figure 6:
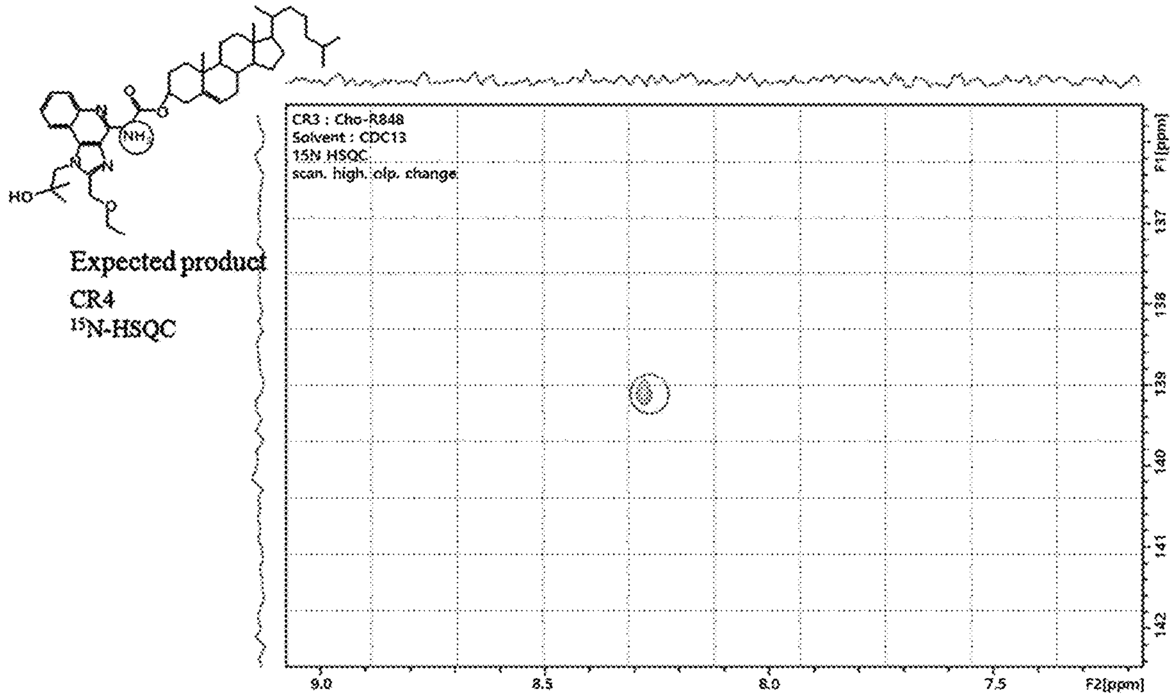
FIG. 6 shows the enlarged result of verifying the structure of the cholesterol-linked toll-like receptor 7/8 agonist according to one embodiment of the present disclosure through $^{15}$N-HSQC.
Figure 7:
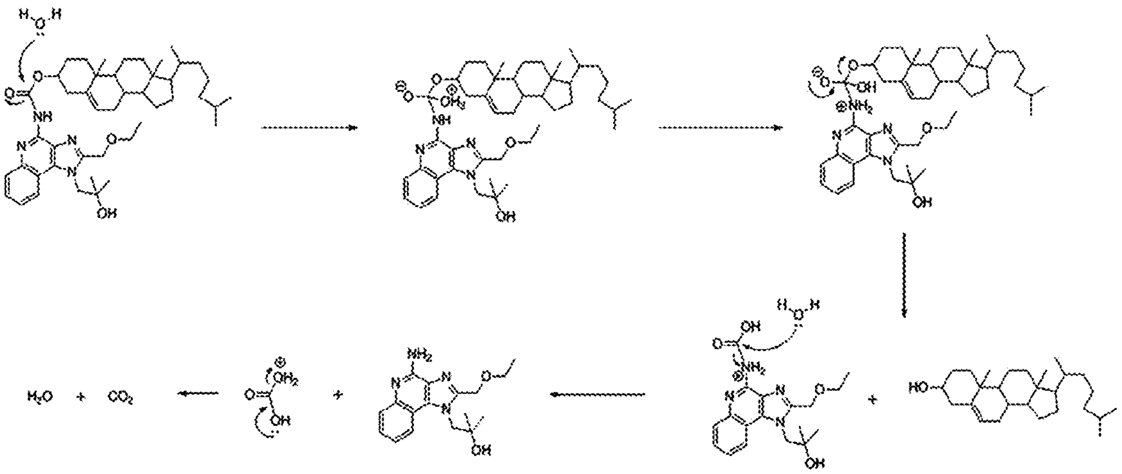
FIG. 7 shows the mechanism of separating the cholesterol-linked toll-like receptor 7/8 agonist according to one embodiment of the present disclosure into cholesterol and a toll-like receptor 7/8 agonist according to a physiological environment in cells.

To synthesize cholesterol-conjugated resiquimod (R848), a method in Reaction Scheme 3 below was used. More specifically, a solution in which 90.0 mg of cholesteryl chloroformate was added and dissolved in 1 mL of dichloromethane was slowly added dropwise to a solution in which 100 μL of pyridine was added to 31.4 mg of resiquimod, and added and dissolved in 3 mL of dichloromethane. Subsequently, a mixture was prepared by stirring the resulting solution at 4° C. for 16 hours. In addition, the mixture was adjusted to room temperature, and distilled water was added to separate water and a dichloromethane layer. Subsequently, sodium sulfate was added to the separated dichloromethane layer, and reacted for 16 hours to remove remaining water. In addition, the remaining solution was purified using a silica gel column, thereby obtaining white cholesterol-conjugated resiquimod powder. The structures of resiquimod used in synthesis and the obtained cholesterol-conjugated resiquimod were verified using $^{1}$H-NMR and $^{15}$N-heteronuclear single quantum coherence (HSQC) spectroscopy. The structures of resiquimod are shown in FIGS. 2 and 4, and the structures of cholesterol-conjugated resiquimod are shown in FIGS. 3, 5 and 6. A separating mechanism of cholesterol from the cholesterol-conjugated resiquimod due to a physiological environment in cells is shown in FIG. 7.

[Reaction Scheme 3]

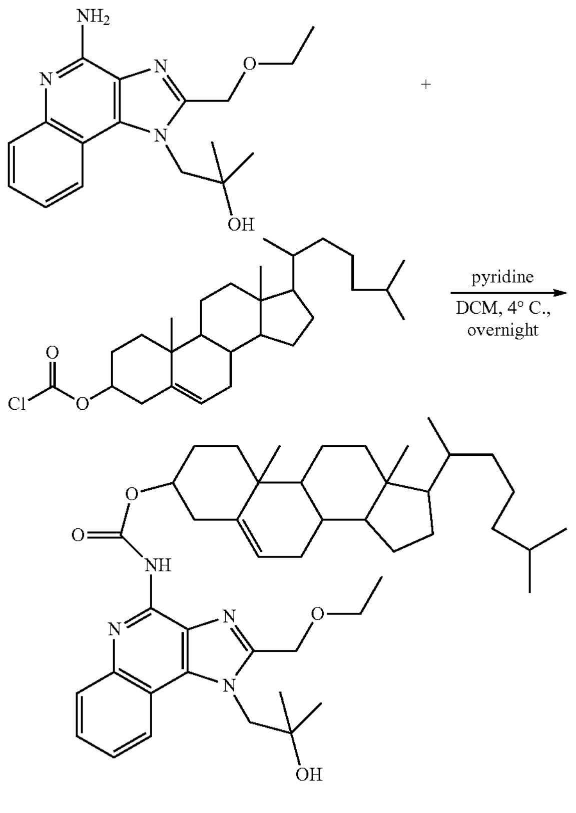

1.2. Synthesis of Imiquimod-Cholesterol Complex Having Carbamate Bond

To synthesize cholesterol-conjugated imiquimod (R837), a method shown in Reaction Scheme 4 below was used. More specifically, a solution in which 90.0 mg of cholesteryl chloroformate was added and dissolved in 1 mL of dichloromethane was slowly added dropwise to a solution in which 100 μL of pyridine was added to 31.4 mg of imiquimod, and then added and dissolved in 3 mL of dichloromethane. Subsequently, a mixture was prepared by stirring the resulting solution at 4° C. for 16 hours. In addition, the mixture was adjusted to room temperature, and then distilled water was added to separate water and a dichloromethane layer, and sodium sulfate was added to the separated dichloromethane layer to allow a reaction for 16 hours so as to remove remaining water. The remaining solution was then purified using a silica gel column, thereby obtaining white powdery cholesterol-conjugated imiquimod.

[Reaction Scheme 4]

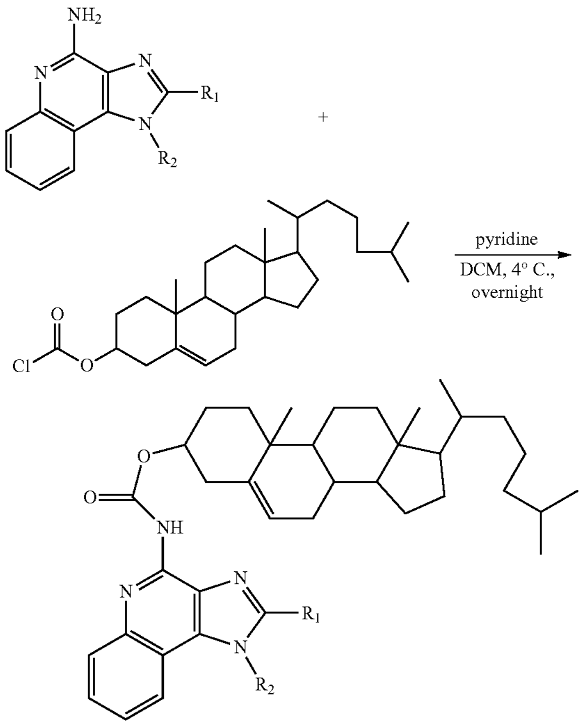

In the above reaction scheme, $R_1$ or $R_2$ is a side chain having an aliphatic or aromatic group, and may include —NH—, —CO—, —CONH—, —CSNH—, —COO—, —CSO—, —$SO_2$NH—, —$SO_2$—, —SO—, and —O—.

Example 2: Synthesis of Toll-Like Receptor 7/8 Agonist-Cholesterol Complex Crosslinked by Disulfide 2.1. Synthesis of Resiquimod-Cholesterol Complex Crosslinked by Disulfide To synthesize resiquimod crosslinked with cholesterol-disulfide, a method of Reaction Scheme 5 below was used. More specifically, 1.54 g of 2-hydroxyethyl disulfide was added and dissolved in 30 mL of tetrahydrofuran, and then slowly added dropwise to a phosgene solution (15 mL, 15 wt % in toluene), thereby preparing a mixture. In addition, the mixture was stirred at 25° C. for 10 hours, and then evaporated the solvent in vacuo. In addition, 2.3 g of N-hydrosuccinimide was added and dissolved in tetrahydrofuran and mixed with the mixture, followed by adding 1.57 mL of triethylamine. In addition, after a reaction at 40° C. for 16 hours, a precipitate was removed, and then the solvent was evaporated in vacuo. In addition, the resulting solution was purified by silica gel column chromatography and recrystallized using cold hexane, and dried in vacuo, thereby obtaining a white solid, which is a purified disulfide-crosslinked linker. In addition, 387 mg of cholesterol was added and dissolved in 10 mL dichloromethane, 523 mg of a disulfide-crosslinked linker was added and stirred at room temperature for 16 hours, and then white cholesterol-disulfide powder, in which cholesterol and disulfide are linked was purified using a silica gel column. In addition, 31.4 mg of resiquimod and 80 mg of cholesterol-disulfide were added to 5 mL dichloromethane, and stirred at room temperature for 16 hours. In addition, distilled water was added to the stirred solution to separate water and a dichloromethane layer, and sodium sulfate was added to the separated dichloromethane layer and reacted for 16 hours so as to remove remaining water. In addition, the remaining solution was purified using a silica gel column, thereby obtaining white cholesterol-disulfide-crosslinked resiquimod powder.

[Reaction Scheme 5]

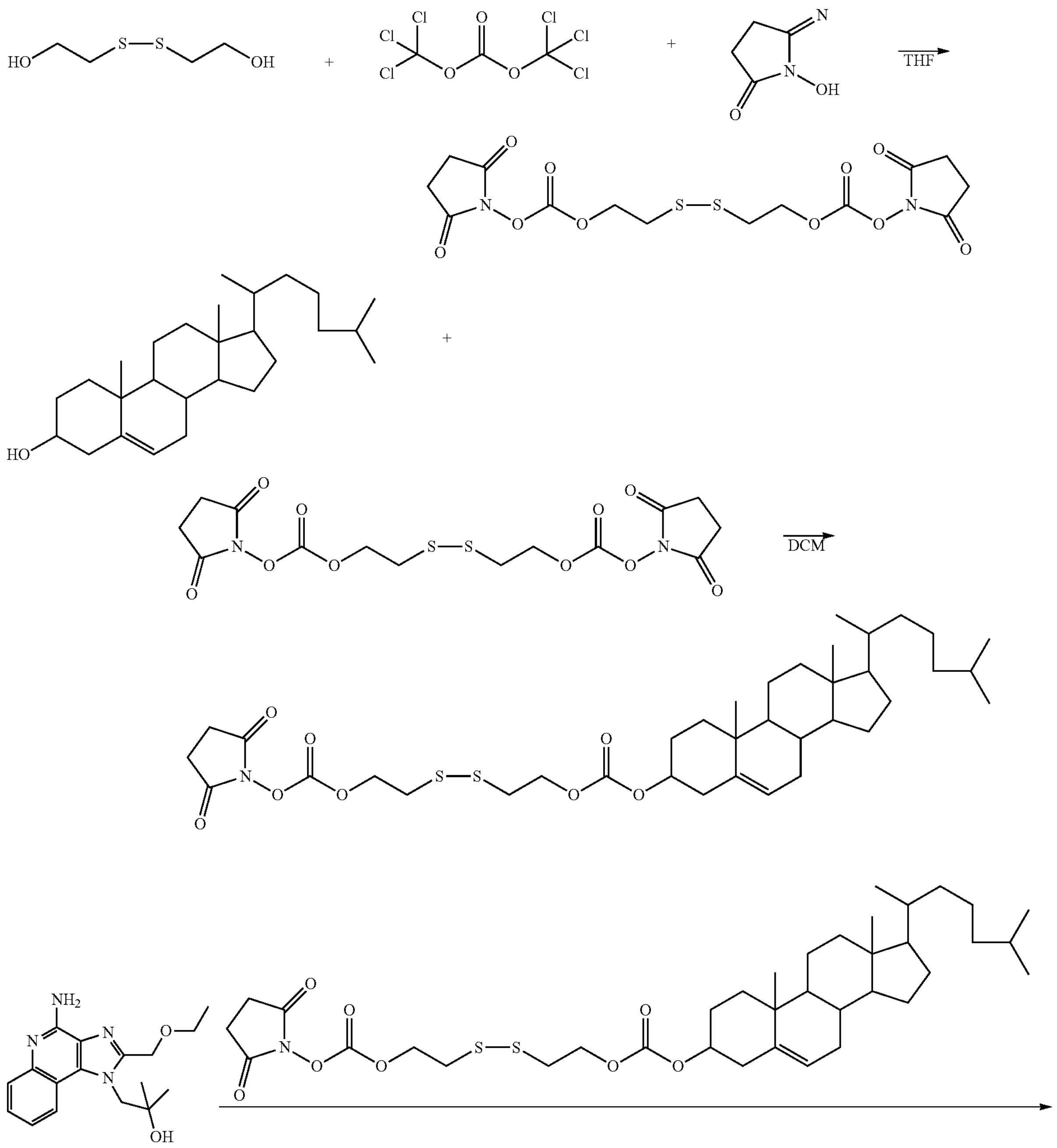

-continued

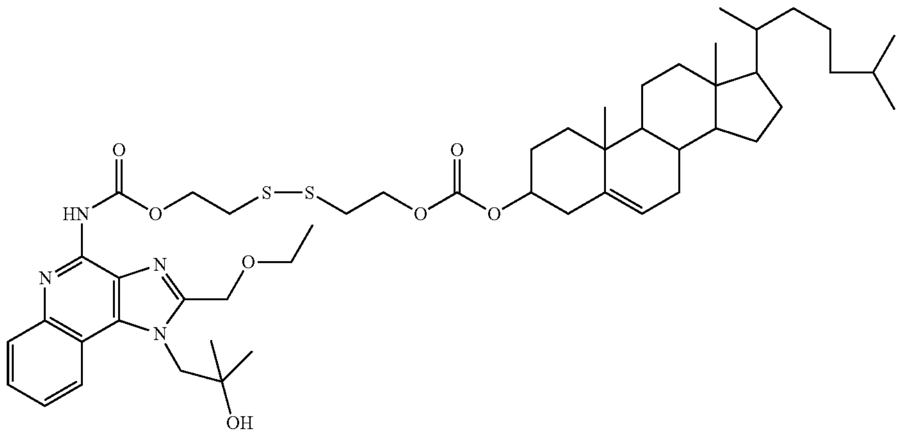 [SMILES: CCOCc1nc2c(NC(=O)OCCSSCCOC(=O)OC3CCC4(C)C(=CCC5C4CCC4(C)C(C(C)CCCC(C)C)CCC54)C3)nc3ccccc3c2n1CC(C)(C)O]

Figure 8:
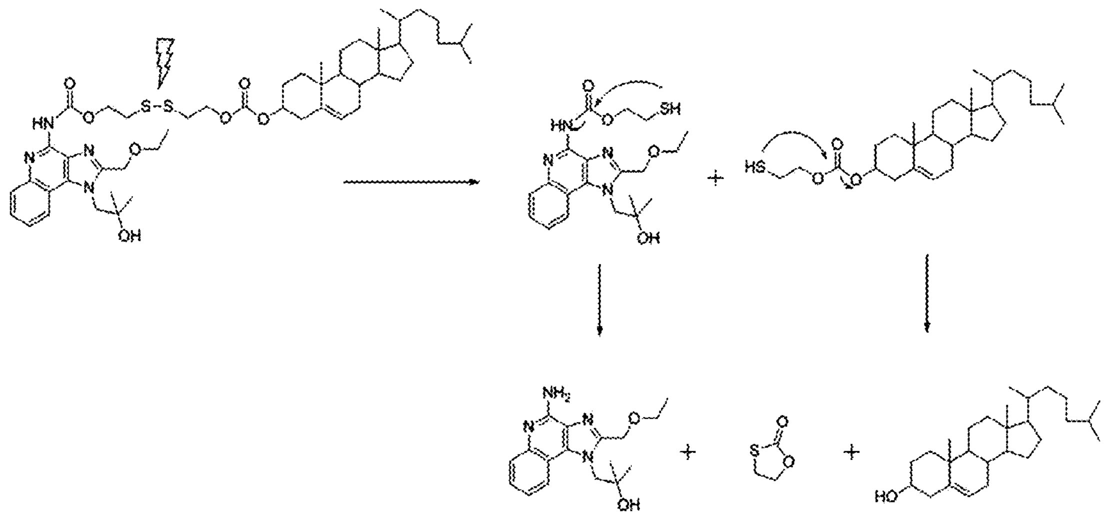
FIG. 8 shows the mechanism of separating the cholesterol-disulfide crosslinked toll-like receptor 7/8 agonist according to one embodiment of the present disclosure from cholesterol due to a physiological environment in cells.

A separating mechanism of cholesterol from the cholesterol-disulfide-crosslinked resiquimod due to a physiological environment in cells is shown in FIG. 8.

2.2. Synthesis of Disulfide-Crosslinked Imiquimod-Cholesterol Complex

To synthesize cholesterol-disulfide-crosslinked imiquimod, a method of Reaction Scheme 6 was used. More specifically, 1.54 g of 2-hydroxyethyl disulfide was added and dissolved in 30 mL tetrahydrofuran, and then slowly added dropwise to a phosgene solution (15 mL, 15 wt % in toluene), thereby preparing a mixture. In addition, the mixture was stirred at 25° ° C. for 10 hours, and then evaporated the solvent in vacuo. In addition, 2.3 g of N-hydrosuccinimide was added and dissolved in tetrahydrofuran, and mixed with the mixture, followed by adding 1.57 mL triethylamine. In addition, after a reaction at 40° C. for 16 hours, a precipitate was removed, and then the solvent was evaporated in vacuo. In addition, the resulting solution was purified by silica gel column chromatography and recrystallized using cold hexane, and dried in vacuo, thereby obtaining a white solid, which is a purified disulfide-crosslinked linker. In addition, 387 mg of cholesterol was added and dissolved in 10 mL dichloromethane, 523 mg of a disulfide-crosslinked linker was added and stirred at room temperature for 16 hours, and then white cholesterol-disulfide powder in which cholesterol and disulfide were conjugated was purified using a silica gel column. In addition, 31.4 mg of imiquimod and 80 mg of cholesterol-disulfide were added to 5 mL dichloromethane, and stirred at room temperature for 16 hours. In addition, distilled water was added to the stirred solution to separate water and a dichloromethane layer, and sodium sulfate was added to the separated dichloromethane layer and reacted for 16 hours to remove remaining water. In addition, the remaining solution was purified using a silica gel column, thereby obtaining white cholesterol-disulfide-crosslinked imiquimod powder.

[Reaction Scheme 6]

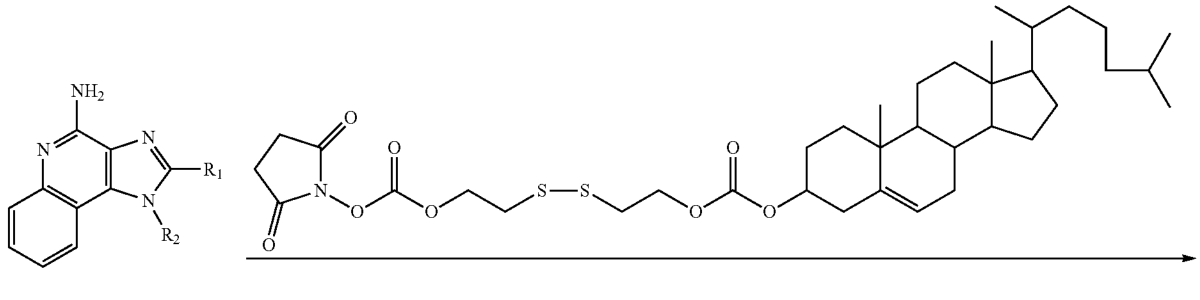

-continued

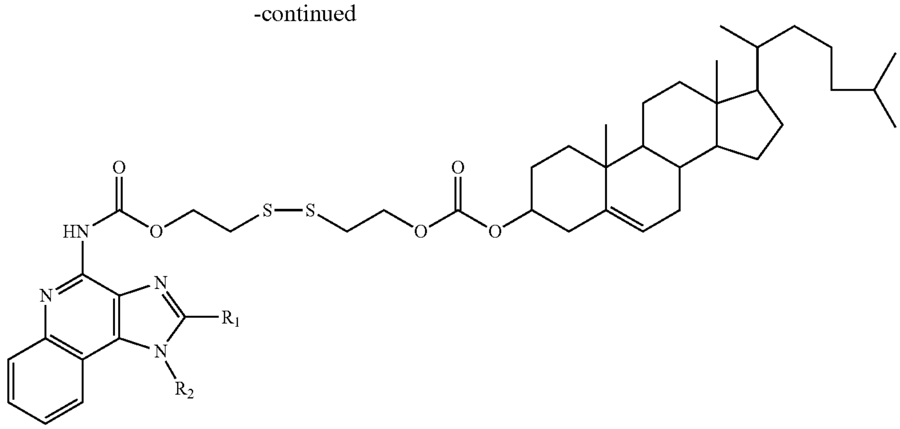

In the above reaction scheme, $R_1$ or $R_2$ is a side chain having an aliphatic or aromatic group, and may include —NH—, —CO—, —CONH—, —CSNH—, —COO—, —CSO—, —$SO_2$NH—, —$SO_2$—, —SO—, and —O—.

Figure 9:
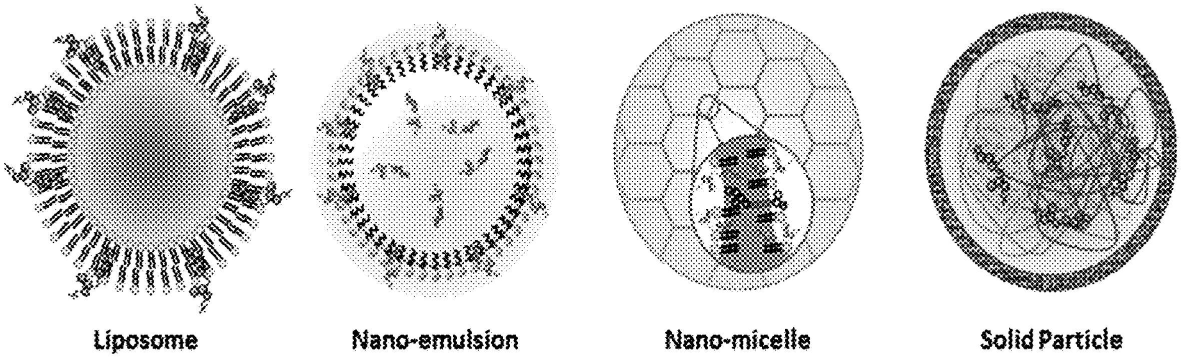
FIG. 9 is a set of schematic diagrams illustrating the shapes of the nanoparticle including the cholesterol-toll-like receptor 7/8 agonist complex.

Example 3: Preparation of Nanoparticles Including Cholesterol-Toll-Like Receptor 7/8 Agonist Complex To maximize the interaction with immune cells, a cholesterol-toll-like receptor 7/8 agonist complex may be prepared in various forms of nanoparticles (FIG. 9).

3.1. Preparation of Nanoliposome Including Cholesterol-Conjugated Resiquimod

To prepare an anionic nanoliposome including cholesterol-conjugated resiquimod, 4 mg of 1,2-dioleoyl-sn-glycero-3-phosphocholine (DOPC, Avanti), 1.2 mg of cholesterol-conjugated resiquimod, and 1 mg of 1,2-dipalmitoyl-sn-glycero-3-phospho-(1'-rac-glycerol) (DPPG, Avanti) were added and dissolved in 1 mL of chloroform, thereby preparing a mixture. The mixture was prepared in a thin film form by evaporating the solvent using a rotary evaporator, and 2 mL of phosphate-buffered saline was added to the thin film, and stirred at 45° C. for 30 minutes, thereby preparing an anionic nanoliposome including cholesterol-conjugated resiquimod through homogenization using a tip sonicator (amplitude: 20%, 2 min). To prepare a cationic nanoliposome including cholesterol-conjugated resiquimod, 4 mg of DOPC, 1.2 mg of cholesterol-conjugated resiquimod, and 2 mg of dimethyloctadecylammonium bromide (DDAB) were added and dissolved in 1 mL of chloroform, thereby preparing a mixture. The mixture was prepared in a thin film form by evaporating the solvent using a rotary evaporator, and 2 mL of phosphate-buffered saline was added to the thin film, and stirred at 45° C. for 30 minutes, thereby preparing a cationic nanoliposome including cholesterol-conjugated resiquimod through homogenization using a tip sonicator (amplitude: 20%, 2 min).

3.2. Preparation of Nanoemulsion Including Cholesterol-Conjugated Resiquimod

To prepare a nanoemulsion including cholesterol-conjugated resiquimod, 1 mg of DOPC, 240 μg of cholesterol, and 240 μg of cholesterol-conjugated resiquimod were added and dissolved in 1 mL of chloroform, thereby preparing a mixture. In addition, the mixture was prepared in the form of a thin lipid film by containing the mixture in a round-bottom flask and completely evaporating chloroform using a rotary evaporator. In addition, squalene (5% v/v), Tween 80 (0.5% v/v) and Span 85 (0.5% v/v) were added and dissolved in 2 mL of phosphate-buffered saline, and the solution was added over the lipid film, dispersed using a tip sonicator for 1 minute, and stirred using a tube revolver for approximately 2 hours, thereby preparing a nanoemulsion including cholesterol-conjugated resiquimod, and then stored at 4° C. in a refrigerator until use.

3.3. Preparation of Nanomicelle Consisting of Cholesterol-Conjugated Resiquimod and Saponin To prepare a nanomicelle consisting of cholesterol-conjugated resiquimod and saponin, phosphatidylcholine, saponin and cholesterol-conjugated resiquimod were mixed in a weight ratio of 5:3:2, and ether was added and dissolved in the mixture to have a concentration of 14 mg/mL, thereby preparing an ether solution including a lipid. In addition, saponin was dissolved in 4 mL distilled water at a concentration of 1.5 mg/mL, and contained in a 20 mL glass bottle. The glass bottle was closed with a rubber stopper, and then stored in a 55° C. water jacket. In addition, 1 mL of the lipid-containing ether solution was added to the glass bottle containing saponin at a rate of 0.2 mL/min using a syringe pump, and stirred for 2 hours. Here, the tip of a syringe needle was placed below the surface of the saponin-containing aqueous solution, and a second needle was inserted into the rubber stopper for ventilation. In addition, the glass bottle was transferred at room temperature, stirred for 3 hours to stabilize, thereby preparing the nanomicelle consisting of cholesterol-conjugated resiquimod and saponin.

3.4. Preparation of Polymer Nanoparticle Consisting of Cholesterol-Conjugated Resiquimod 60 mg of a PLGA polymer (Eudragit) having a composition ratio of lactide and glycolide of 50:50 was dissolved in 1 mL of a chloroform solvent. 5 mg of cholesterol-conjugated resiquimod was added to the solvent and the cholesterol-resiquimod complex and the polymer were dissolved using a sonicator (ultrasonic bath, Emerson Model CPX5800H-E). In addition, the resulting solution was added to 10 mL of a 2.5% PVA aqueous solution by 200 μL, and dispersed for 1 minute using a tip sonicator (Sonics & Materials Model VCX 750). Here, the output of a disperser was 750 watts, a vibration intensity was 20 kHz, and an amplitude was set to 20%. In addition, to completely evaporate the PLGA-dissolved organic solvent, the prepared aqueous solution was stirred at 600 rpm and room temperature for 8 hours or more. To remove the unreacted polymer and cholesterol-resiquimod complex, centrifugation was performed at 12,000 rpm for 12 minutes using a centrifuge (Hanil, Combi-514R), a supernatant was removed, 10 mL of deionized water was added, and then the resulting solution was dispersed in a sonicator for 30 seconds. The above-described process was repeated three times, followed by drying by lyophilization and storing at −20° C.

Example 4: Characterization of Nanoparticles Including Cholesterol-Toll-Like Receptor 7/8 Agonist Complex and Evaluation of Immune Activating Efficacy of Immune Cells After nanoparticles including the cholesterol-toll-like receptor 7/8 agonist complex of the present disclosure were delivered into cells, it was confirmed whether cholesterol and resiquimod were separated under acidic conditions in the cytoplasm. More specifically, nanoliposomes including cholesterol-conjugated resiquimod were prepared by the same method as in Example 3.1, 10 μg of the prepared nanoliposome was added to 1 mL of phosphate-buffered saline (PBS) having pH 5 or 7 at 37° C. In addition, each sample was obtained on day 0.5, 1, 1.5 or 2 to measure a concentration of separated resiquimod using a UV-Vis spectrum. The result is shown in FIG. 10.

Figure 10:
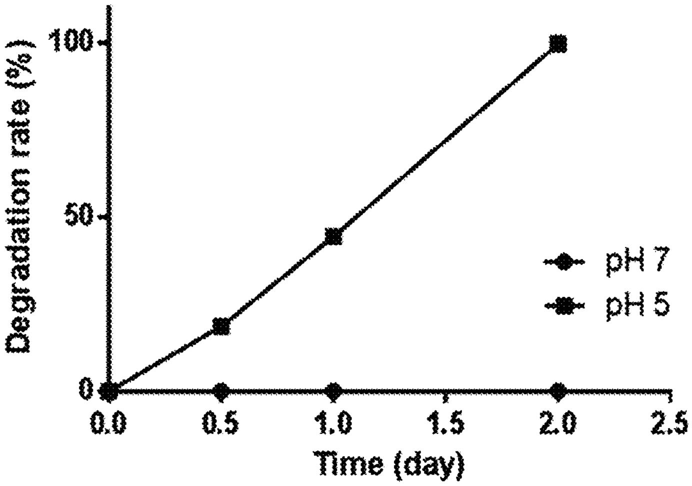
FIG. 10 is a graph showing the result of confirming that the toll-like receptor 7/8 agonist-cholesterol complex according to one embodiment of the present disclosure is kinetically separated over time at a constant pH.

As shown in FIG. 10, while resiquimod and cholesterol were not separated at pH 7, it was confirmed that resiquimod is separated from cholesterol over time at pH 5. According to the result, after the nanoparticles including the cholesterol-toll-like receptor 7/8 agonist complex were delivered into the cytoplasm in the body, it was confirmed that the toll-like receptor 7/8 agonist is separated from cholesterol to induce an immune activating reaction in the cytoplasm.

In addition, to confirm whether cleavage is made by a specific enzyme present in a tumor microenvironment excluding pH, a nanoliposome including cholesterol-conjugated resiquimod was prepared by the same method as Example 3.1, 30 units of carboxylesterase were treated and reacted at 37° C. In addition, cholesterol cleavage was confirmed. The result is shown in FIG. 11.

Figure 11:
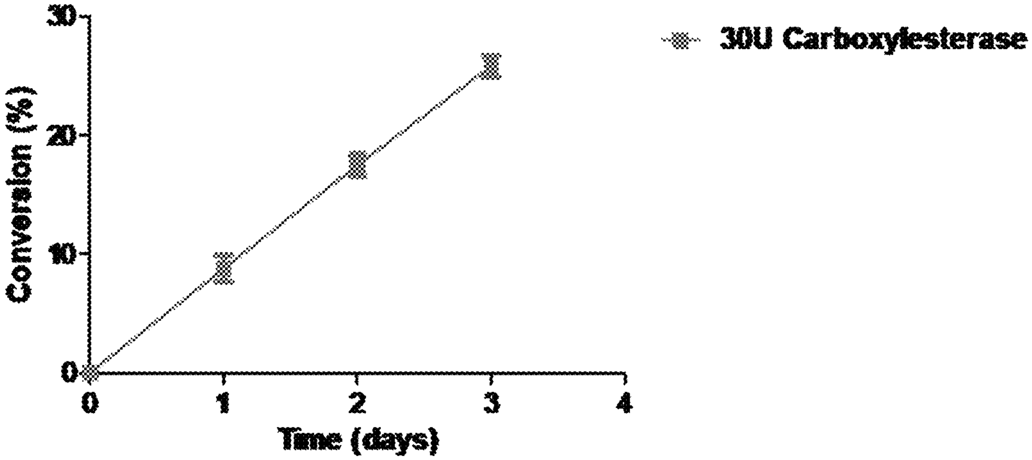
FIG. 11 is a graph showing the result of confirming that the toll-like receptor 7/8 agonist-cholesterol complex according to one embodiment of the present disclosure is kinetically separated over time due to an enzyme.

As shown in FIG. 11, it was confirmed that the cholesterol of the cholesterol-toll-like receptor 7/8 agonist complex was cleaved by a specific enzyme present in cells of a tumor microenvironment.

To confirm cytotoxicity, $10^4$ Raw264.7 macrophages were treated with 100 μL each of 500 ng/mL and 1,000 ng/mL of liposomes, nanoliposomes including a cholesterol-resiquimod complex, and resiquimod, and reacted for 24 hours. In addition, a cell survival rate was measured using CellTiter 96 AQueous One Solution Cell Proliferation Assay (Promega). As a negative control, an experiment was carried out using phosphate-buffered saline. The result is shown in FIG. 12.

Figure 12:
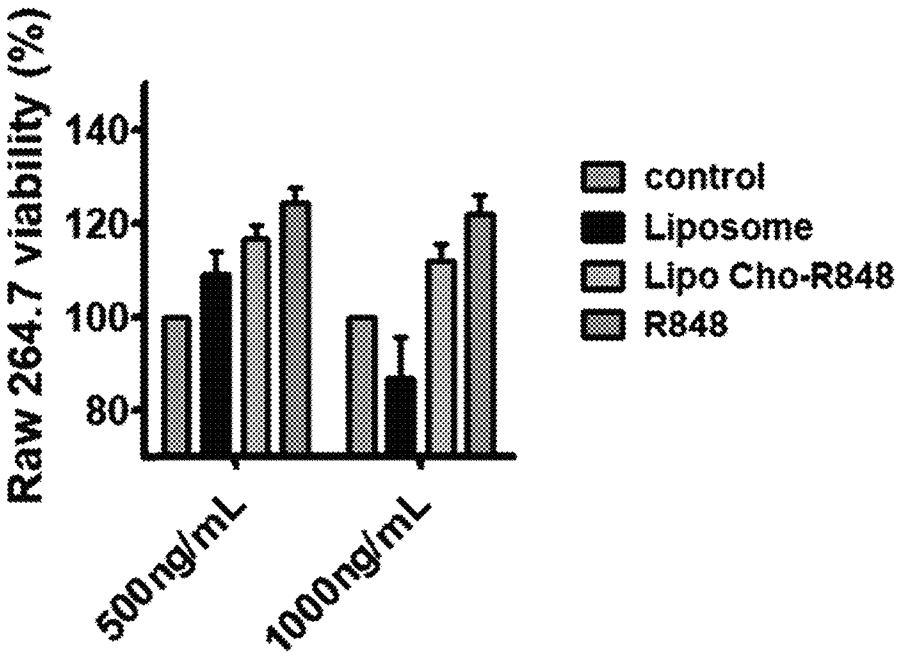
FIG. 12 is a graph showing the result of confirming the cytotoxicity of the nanoliposome including the toll-like receptor 7/8 agonist-cholesterol complex according to one embodiment of the present disclosure.

As shown in FIG. 12, it was confirmed that the nanoliposomes including the cholesterol-resiquimod complex not only exhibits cytotoxicity, but also exhibits an effect of promoting proliferation by immune cell activation.

In addition, to confirm the degree of immune cell activation, $10^6$ Raw264.7 macrophages were treated with 1 mL each of 500 ng/mL and 1,000 ng/mL of liposomes, nanoliposomes including the cholesterol-resiquimod complex and resiquimod, and incubated for 24 hours, thereby obtaining a liquid cell culture. The liquid cell culture was centrifuged at 1,500 rpm for 10 minutes to obtain a cell-free supernatant, and the concentrations of IL-6 and TNF-α included in the supernatant were measured through ELISA using a BD OptiEIA™ kit. The result is shown in FIGS. 13 and 14.

Figure 13:
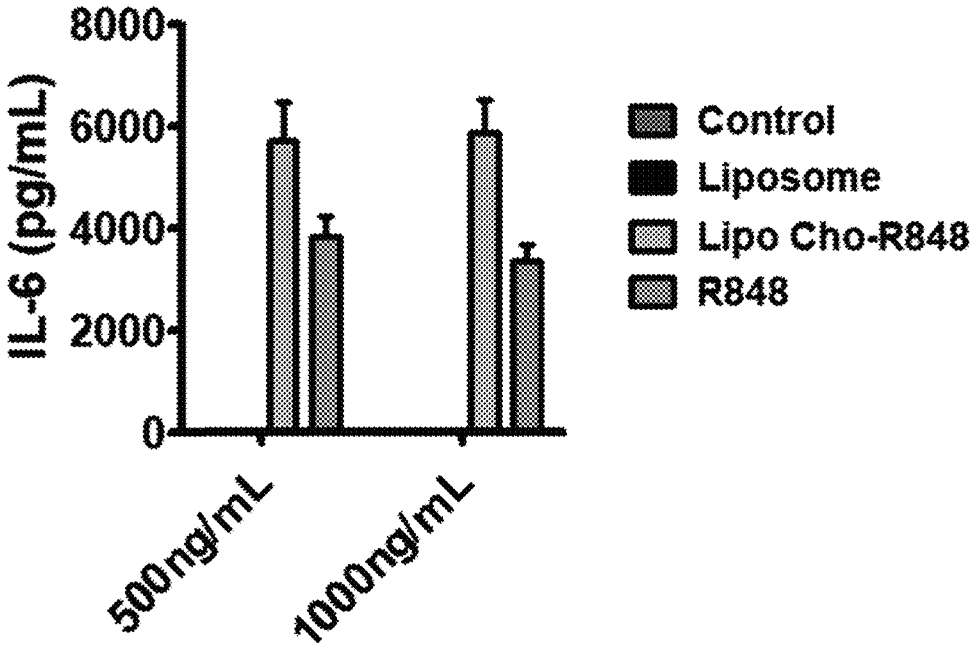
FIG. 13 is a graph showing the result of confirming an immune cell activation indicator (IL-6) of the nanoliposome including the toll-like receptor 7/8 agonist-cholesterol complex according to one embodiment of the present disclosure.
Figure 14:
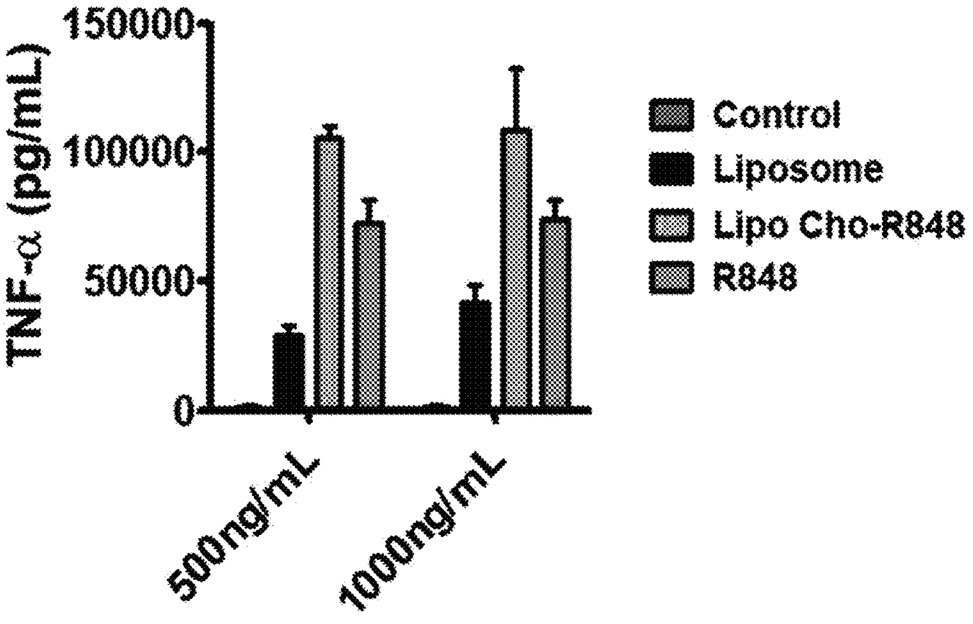
FIG. 14 is a graph showing the result of confirming an immune cell activation indicator (TNF-alpha) of the nanoliposome including the toll-like receptor 7/8 agonist-cholesterol complex according to one embodiment of the present disclosure.

As shown in FIGS. 13 and 14, compared to when resiquimod was treated alone, it was confirmed that IL-6 and TNF-α release amounts increase in an experimental group treated with the nanoliposomes including the cholesterol-resiquimod complex, demonstrating that the immune activation of a toll-like receptor 7/8 agonist may not only be stably induced at a desired point of time in cells, but also increase the degree of immune activation, using the nanoliposomes including the cholesterol-toll-like receptor 7/8 agonist complex.

Degree of activation of immune cells was confirmed using the cholesterol-resiquimod complex, in which cholesterol is not cleaved at a specific point of time as a control. More specifically, $2\times10^5$ cells/mL of bone marrow-derived dendritic cells (BMDCs) or bone marrow-derived macrophages (BMDMs) were treated with each of a liposome (Lipo(Chol-R848)) including the cholesterol-resiquimod complex of the present disclosure, a liposome (Lipo(C18-R848)) including an uncleaved cholesterol-resiquimod complex, a liposome and resiquimod by concentration, and incubated for 24 hours. In addition, a liquid culture was obtained, centrifuged at 490 g for 5 minutes, thereby obtaining only a supernatant, and ELISA was carried out using a BD OptEIA™ kit. The result is shown in FIG. 15.

Figure 15:
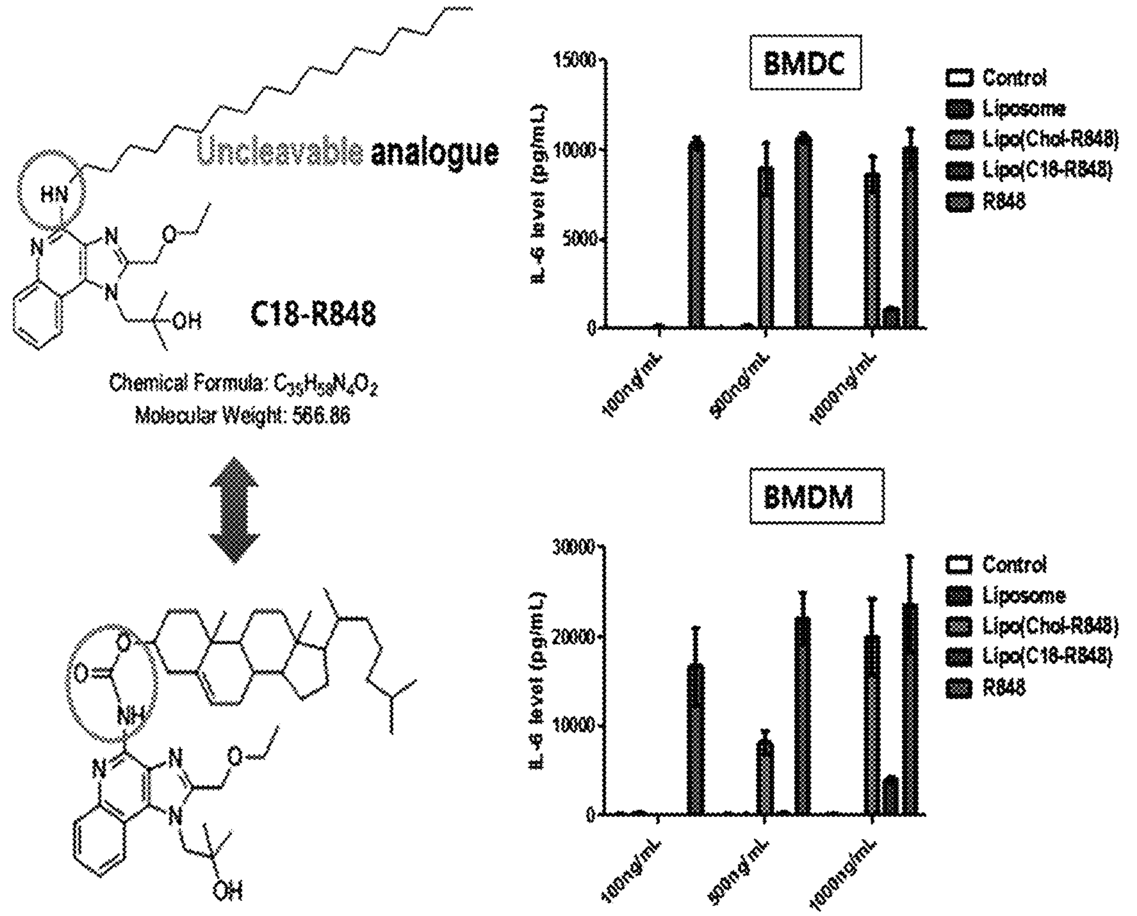
FIG. 15 shows the difference in activation of immune cells by a Chol-R848 material synthesized to allow cleavage at a binding site of the toll-like receptor 7/8 agonist-cholesterol complex according to one embodiment of the present disclosure and a C18-R848 material synthesized to prevent cleavage thereof.

As shown in FIG. 15, while the cholesterol-toll-like receptor 7/8 agonist complex of the present disclosure effectively activates immune cells by inducing the cleavage of cholesterol in the cytoplasm, it was confirmed that the complex, in which cholesterol cleavage is not induced does not activate immune cells since the active site of resiquimod is not exposed. From the above results, it was confirmed that the cholesterol-toll-like receptor 7/8 agonist complex of the present disclosure is inactivated when cholesterol is not cleaved, but effectively activates immune cells after cholesterol is cleaved under a specific condition, thereby regulating an immune response.

Example 5: Evaluation of Immune Activation in Lymph Node and Toxic Effect in Serum after In Vivo Injection of Cholesterol-Toll-Like Receptor 7/8 Agonist To confirm an effect of the cholesterol-toll-like receptor 7/8 agonist complex in vivo, an in vivo experiment was carried out. More specifically, a liposome including the cholesterol-resiquimod complex or resiquimod (free drug) was subcutaneously injected into the right flank of a C57BL/6 mouse at 25 μg/100 μL. In addition, after 1, 4 and 8 days, a lymph node was separated from the mouse, followed by cryosection. In addition, dendritic cells and macrophages were labeled with a CD205 antibody and CD169 antibody, respectively, which was detected using a fluorescent microscope. The result is shown in FIG. 16.

Figure 16:
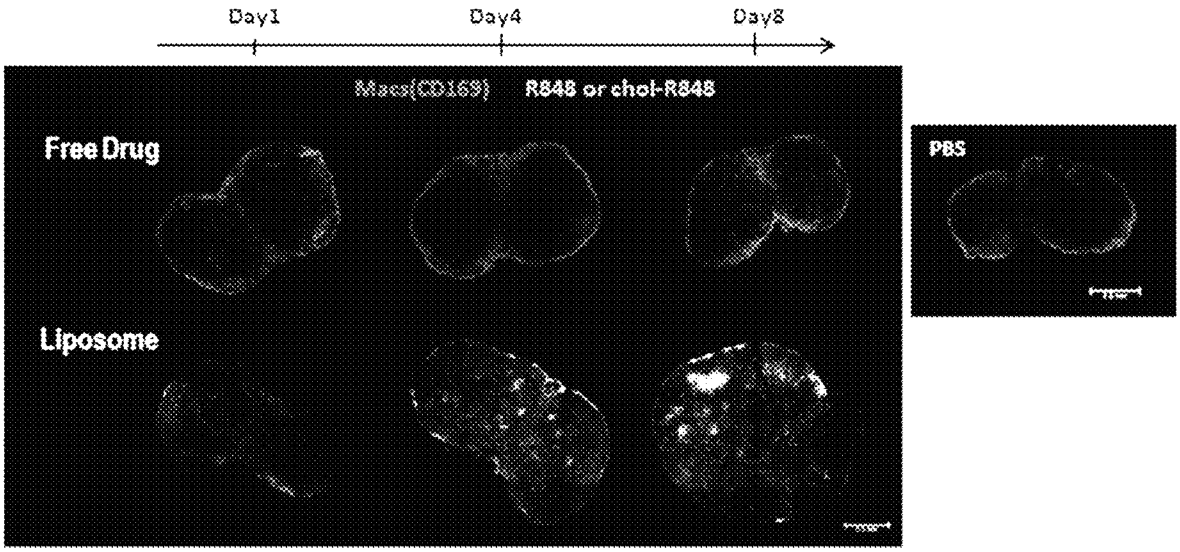
FIG. 16 shows the result of confirming an amount reaching a lymph node and a retention time after the nanoliposome including resiquimod and the toll-like receptor 7 or 8 agonist-cholesterol complex according to one embodiment of the present disclosure are injected into the body.

As shown in FIG. 16, while the activation of immune cells in a lymph node is not induced in the case of mice treated with resiquimod alone, it was confirmed that immune cells are activated in a lymph node in the case of mice treated with the liposome including the cholesterol-resiquimod complex.

In addition, to confirm the long-term in vivo effect of the cholesterol-toll-like receptor 7/8 agonist complex, a liposome (Lipo(Chol-R848)) including the cholesterol-resiquimod complex, a liposome or resiquimod (R848) was subcutaneously injected into the right flank of C57BL/6 mice at 25 μg/100 μL, and then lymph nodes were obtained according to treatment time until 15 days. In addition, the obtained lymph nodes were first physically fragmented using scissors, treated with 1 mg/mL of collagenase D, reacted for 1 hour for second lysis, and then filtered using a 70 μm strainer, followed by separating the cells and a supernatant using a centrifuge (490 g, 5 min). In addition, the obtained cells were labeled with a CD11c antibody and CD11b antibody, and fixed using 4% paraformaldehyde. In addition, analysis was carried out using a BD FACS Canto II flow cytometer. In addition, the separated supernatant was analyzed through ELISA to measure an amount of cytokine IL-12. The result is shown in FIG. 17A.

Figure 17A:
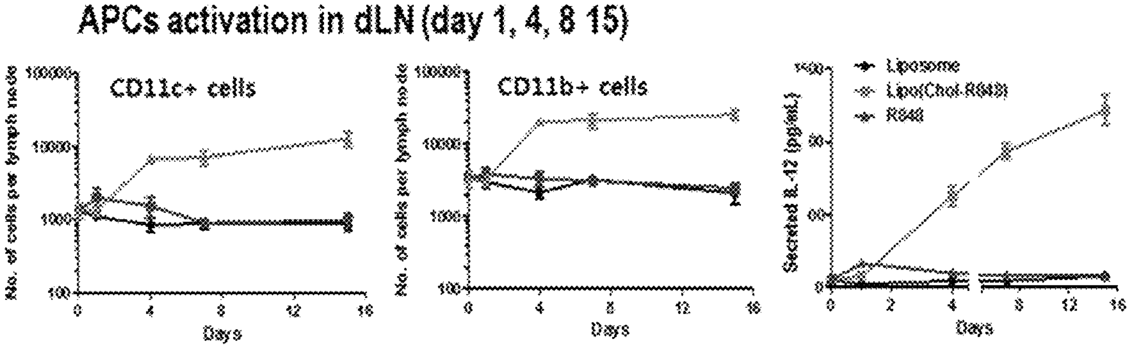
FIGS. 17A and 17B show the result of confirming the immune cell activation efficacy and toxicity of a nanoliposome including the toll-like receptor 7/8 agonist-cholesterol complex according to one embodiment of the present disclosure.

As shown in FIG. 17A, while the activation of immune cells was not induced in mice treated with a liposome or resiquimod alone, it was confirmed that in the experimental group treated with nanoparticles including the cholesterol-toll-like receptor 7/8 agonist complex of the present disclosure, the number of immune cells in a lymph node gradually increased, and immune cells were effectively activated, thereby stably releasing a cytokine for a long time.

In addition, to confirm toxicity in vivo, a liposome (Lipo(Chol-R848)) including the cholesterol-resiquimod complex, a liposome or resiquimod (R848) was subcutaneously injected into the right flank of a C57BL/6 mouse at 25 μg/100 μL, the body weight of the mouse was measured, and blood was collected from the orbital vein on each time. In addition, the collected blood was centrifuged (4° C., 13,000 rpm, 20 min) to separate serum and blood cells, and a cytokine amount was measured through ELISA using the serum. The result is shown in FIG. 17B.

Figure 17B:
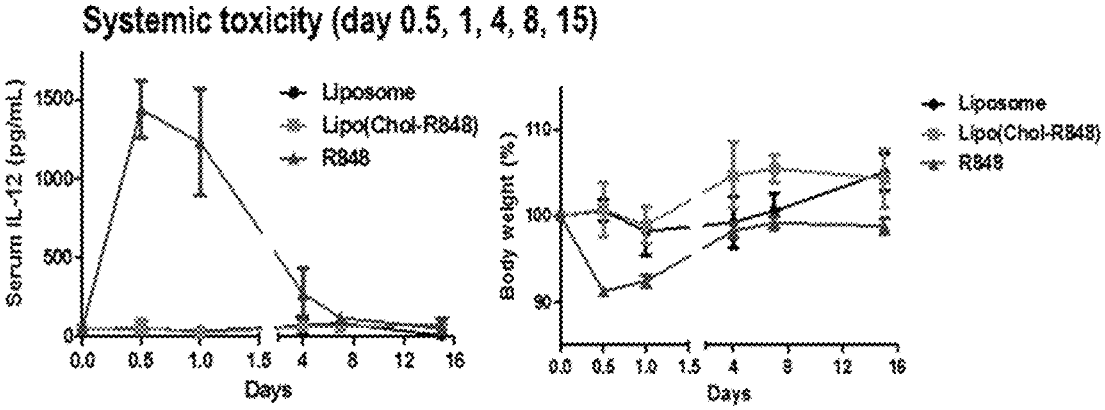

As shown in FIG. 17B, in the experimental group treated with resiquimod alone, a cytokine rapidly increased in serum at an early stage to induce a cytokine storm, thereby dramatically changing a body weight by inducing cytotoxicity, whereas in the case of a nanoparticle including the cholesterol-toll-like receptor 7/8 agonist complex of the present disclosure, a cytokine amount was not changed in serum, and a body weight loss was not observed, confirming no in vivo toxicity.

Example 6: Verification of Anticancer Effect of Cholesterol-Toll-Like Receptor 7/8 Agonist Complex

6.1. Verification of Anticancer Effect of Cholesterol-Toll-Like Receptor 7/8 Agonist Complex and Cancer Antigen To confirm that the cholesterol-toll-like receptor 7/8 agonist complex exhibits an anticancer effect, an experiment was carried out using a B16-OVA melanoma cell line and an ovalbumin (OVA) antigen. More specifically, $5\times10^5$ cells of a B16-OVA cell line were subcutaneously injected into the right flank of a C57BL/6 mouse, and the time when a tumor size reached approximately 50 $mm^3$ was set to day 0, each of phosphate-buffered saline (control), an OVA antigen (OVA), resiquimod+OVA antigen (R848+OVA), and a nanoliposome including a cholesterol-resiquimod complex, +OVA antigen (Lipo(Chol-R848)+OVA) were administered into a mouse through intratumoral injection on day 0, 3, 6 and 9. 10 μg of the OVA antigen was administered, 25 μg of resiquimod was administered, and 25 μg (based on resiquimod) of the nanoliposome including the cholesterol-resiquimod complex was administered. In addition, a mouse survival rate and a cancer size were measured. The result is shown in FIG. 18.

Figure 18:
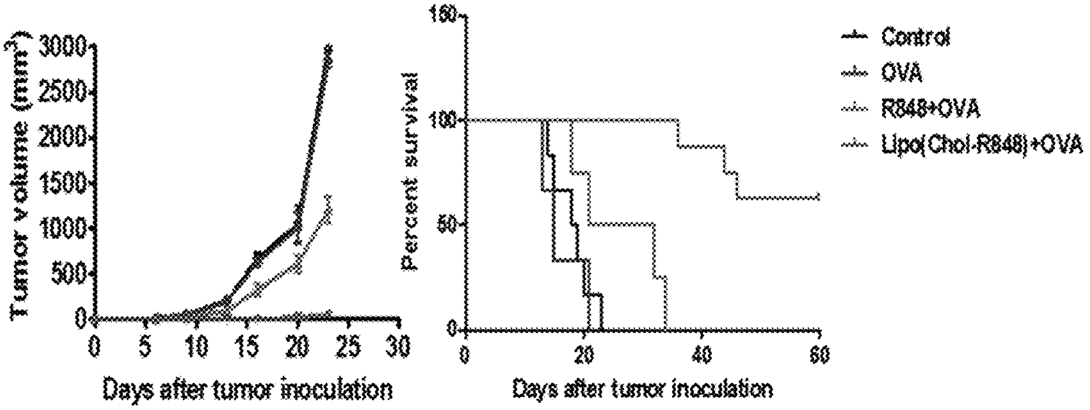
FIG. 18 shows the result of confirming the tumor growth inhibitory effect and survival rate of the nanoliposome including the toll-like receptor 7/8 agonist-cholesterol complex according to one embodiment of the present disclosure.

As shown in FIG. 18, in the experiment group injected only with the OVA antigen, like the control injected with phosphate-buffered saline, a cancer size dramatically increased, and there was no mouse surviving three weeks or more, and in the experimental group injected with resiquimod and an OVA antigen, compared to the control, it was confirmed that a rate of increase in the cancer size is reduced, but the cancer size still increases. However, in the experimental group injected with the nanoparticle including the cholesterol-toll-like receptor 7/8 agonist complex of the present disclosure, it was confirmed that cancer hardly grows, and even after 60 days, a survival rate of approximately 60% or more is shown.

In addition, to confirm an effect on immune cells, in the same manner as above, each of PBS, an OVA antigen and nanoliposome (liposome), resiquimod and an OVA antigen (R848), and a nanoliposome including the cholesterol-resiquimod complex and an OVA antigen (Lipo(Chol-R848)) were administered on day 0, 3, 6 and 9 through intratumoral injection, and 7 days after administration of the final sample, tumor tissue and a spleen were separated from a mouse. In addition, the obtained tumor tissue was primarily fragmented using scissors, the fragmented tissue was treated with 1 mg/mL of collagenase type I, and reacted at 37° C. for 1 hour to separate into single cells. In addition, the separated cells were filtered using a 70 μm strainer, and washed using phosphate-buffered saline. The obtained spleen was primarily fragmented using scissors, treated with a red blood cell lysis buffer, and reacted at 37° C. for 10 minutes to lyse red blood cells. In addition, the cells were filtered using a 70 μm strainer, and washed with phosphate-buffered saline. The washed tumor cells and spleen cells were labeled with antibodies. T cells were labeled with anti-CD4 antibody and anti-CD8 antibody, type 2 macrophages (M2 macrophages) were labeled with anti-CD11b antibody and anti-CD206 antibody, myeloid-derived suppressor cells (MDSCs) were labeled with anti-CD11b antibody and anti-Gr1 antibody, and natural killer cells (NK cells) were labeled with anti-NK1.1 antibody. In addition, these cells were analyzed using a fluorescence flow cytometer. The result is shown in FIGS. 19 and 20.

Figure 19A:
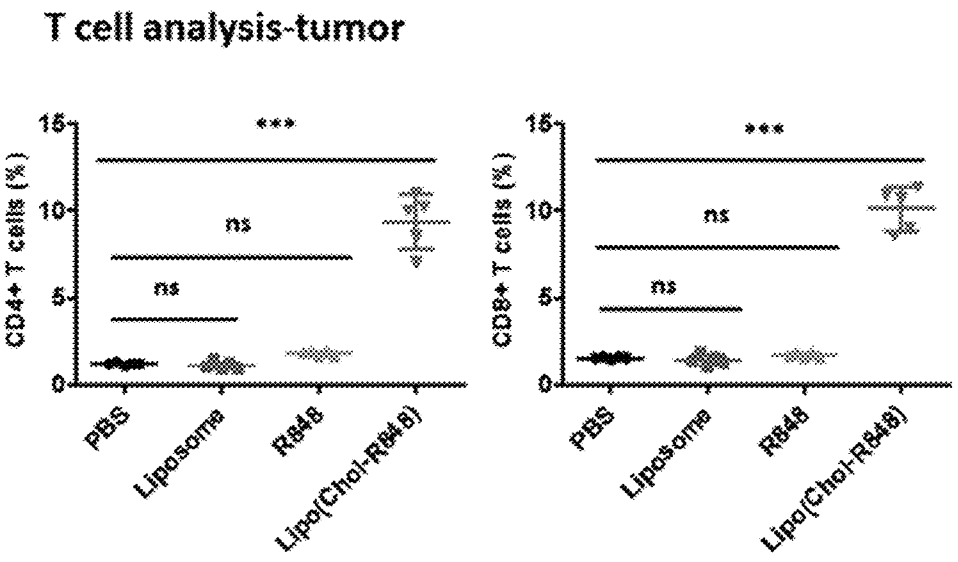
FIGS. 19A and 19B show the result of confirming the ability of regulating immune cell activity of the nanoliposome including the toll-like receptor 7/8 agonist-cholesterol complex according to one embodiment of the present disclosure at a tumor site.
Figure 19B:
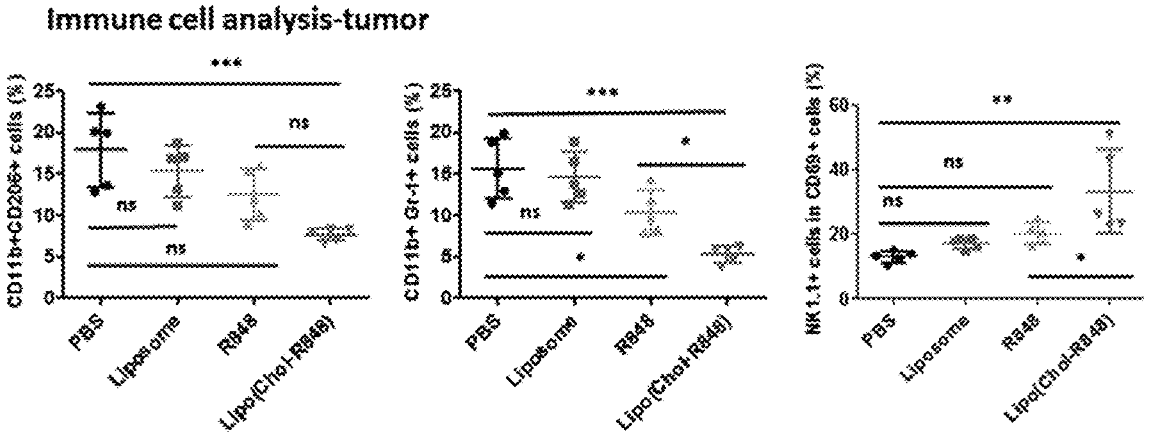
Figure 20A:
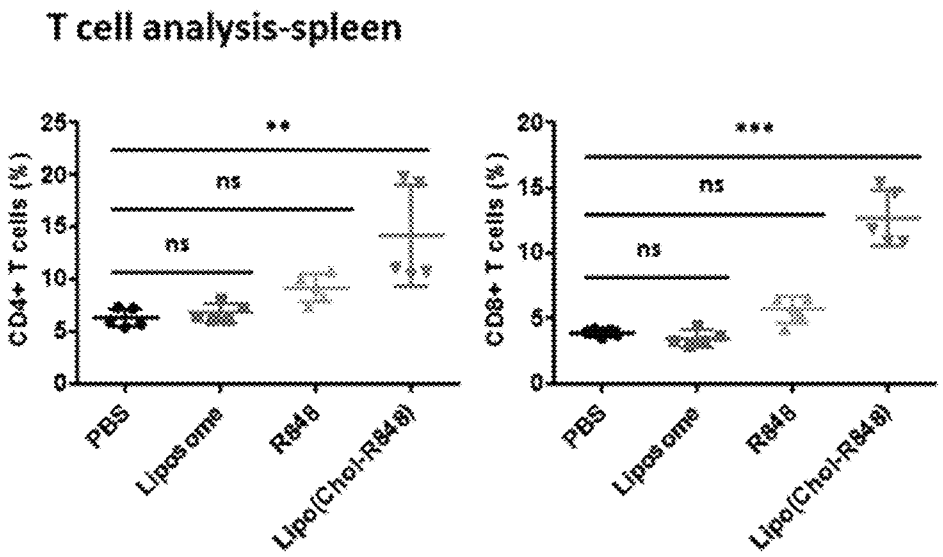
FIGS. 20A and 20B show the result of confirming the ability of regulating immune cell activity of the nanoliposome including the toll-like receptor 7/8 agonist-cholesterol complex according to one embodiment of the present disclosure in the spleen.
Figure 20B:
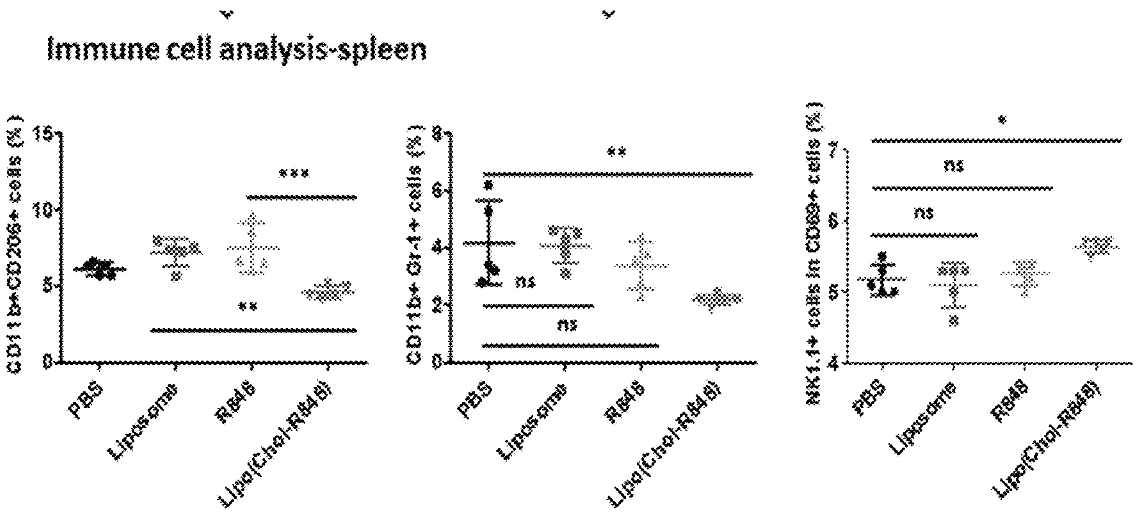

As shown in FIGS. 19 and 20, while, in the experimental group injected with the nanoparticle including the cholesterol-toll-like receptor 7/8 agonist complex, the numbers of CD4+ T cells, CD8+ T cells and NK cells, which exhibit an anticancer effect in tumor tissue, significantly increase, it was confirmed that the numbers of M2 macrophages and MDSC cells, which have an immunosuppressive function, are significantly reduced.

6.2. Verification of Anticancer Effect Caused by Co-Administration of Cholesterol-Toll-Like Receptor 7/8 Agonist Complex and Immune Checkpoint Inhibitor To confirm an anticancer effect of co-treatment of the cholesterol-toll-like receptor 7/8 agonist complex and an immune checkpoint inhibitor, an experiment was carried out with a B16-OVA melanoma cell line, a TC-1 lung cancer cell line, and a 4T1 breast cancer cell line. More specifically, $5\times10^5$ cells of the B16-OVA cell line, TC-1 cell line or 4T1 cell line were subcutaneously injected into the right flank of a C57BL/6 mouse, and after the time when the tumor size reached approximately 50 $mm^3$ was set to day 0, phosphate-buffered saline (PBS); anti-PD-1 and a cancer antigen (α-PD-1); anti-PD-L1 and a cancer antigen (α-PD-L1); a nanoliposome including the cholesterol-resiquimod complex and a cancer antigen (Lipo(Chol-R848)); a nanoliposome including the cholesterol-resiquimod complex, anti-PD-1 and a cancer antigen (Lipo(Chol-R848)+α-PD-1); and a nanoliposome including the cholesterol-resiquimod complex, anti-PD-L1 and a cancer antigen (Lipo(Chol-R848)+α-PD-L1) were administered on day 0, 3, 6 and 9. Anti-PD-1 and anti-PD-L1, which are immune checkpoint inhibitors, were intraperitoneally injected at 100 μg/100 μL on day 0, 3 and 6, and the others were administered through intratumoral injection in the same manner as in Example 5.1. As the cancer antigen, an OVA antigen was used for a B16-OVA animal model, a peptide-based antigen was used for a TC-1 animal model, and a tumor cell lysate was used as an antigen for a 4T1 animal model. In addition, a mouse survival rate and a cancer size were measured. The results are shown in FIGS. 21 to 23.

Figure 21:
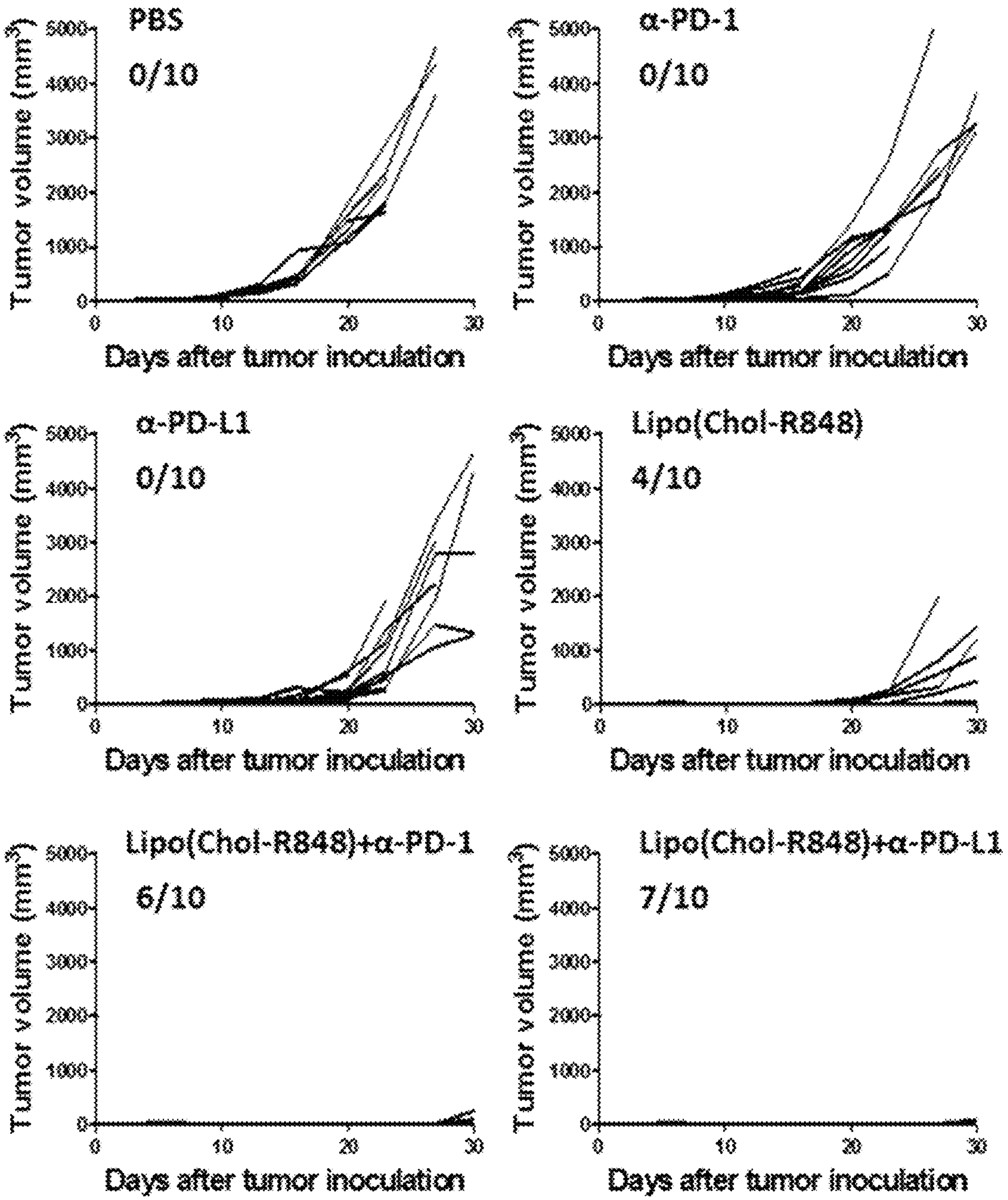
FIG. 21 shows the result of confirming the effect of co-administering the nanoliposome including the toll-like receptor 7/8 agonist-cholesterol complex according to one embodiment of the present disclosure and an immune checkpoint inhibitor in a B16-OVA animal model.
Figure 22A:
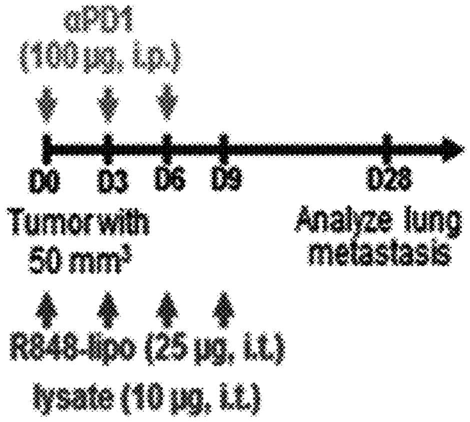
FIGS. 22A to 22E show the result of confirming the effect of co-administering the nanoliposome including the toll-like receptor 7/8 agonist-cholesterol complex according to one embodiment of the present disclosure and an immune checkpoint inhibitor in a 4T1 animal model.
Figure 22B:
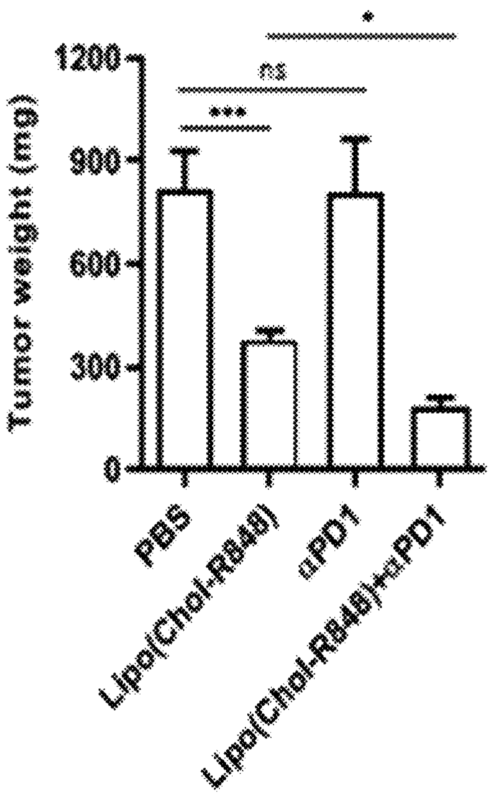
Figure 22C:
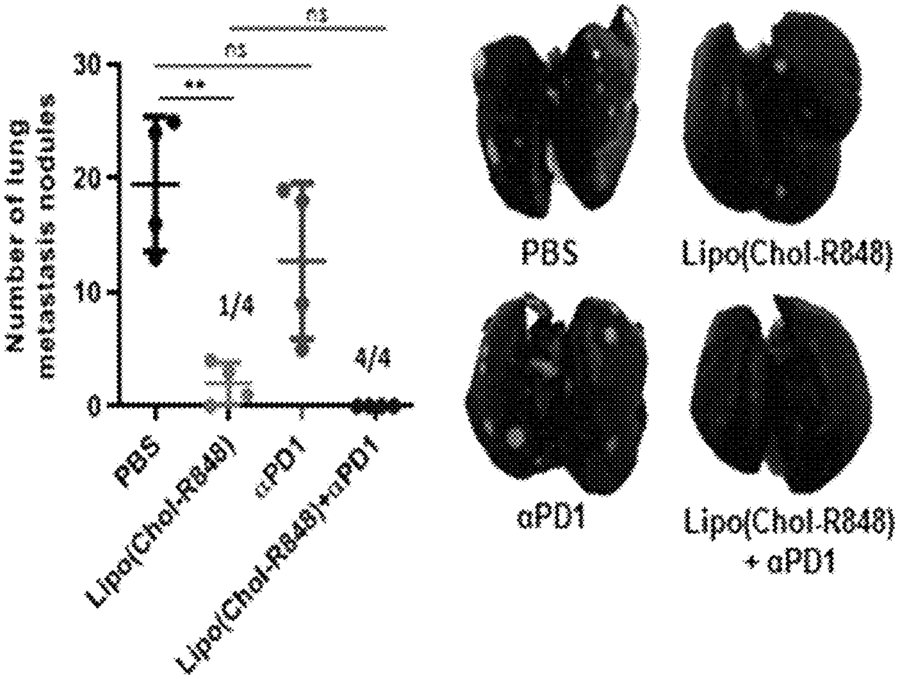
Figure 22D:
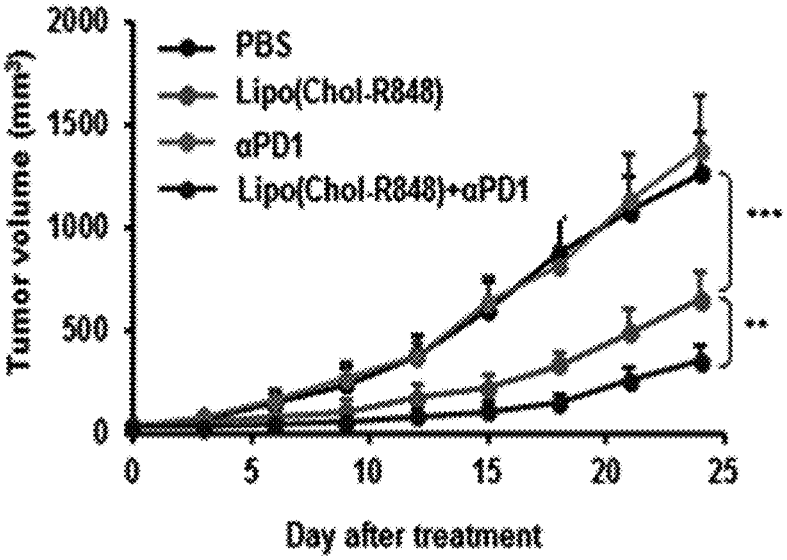
Figure 22E:
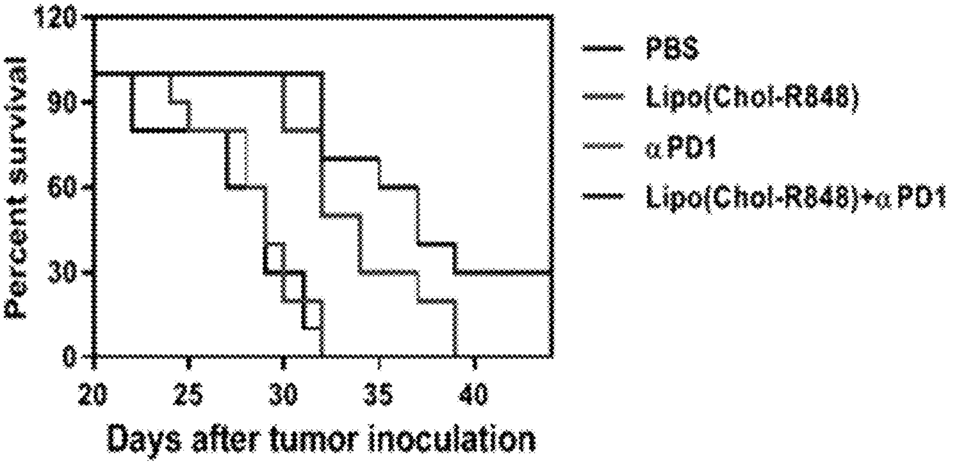
Figure 23A:
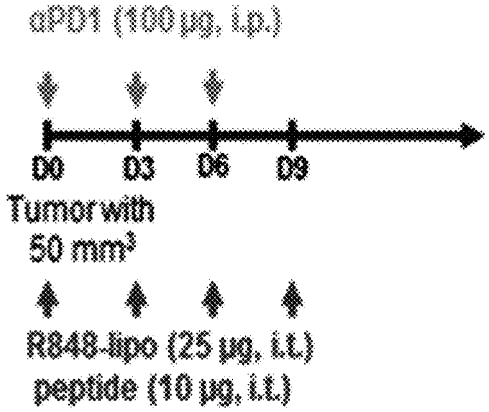
FIGS. 23A-23D show the result of confirming the effect of co-administering the nanoliposome including the toll-like receptor 7/8 agonist-cholesterol complex according to one embodiment of the present disclosure and an immune checkpoint inhibitor in a TC1 animal model.
Figure 23B:
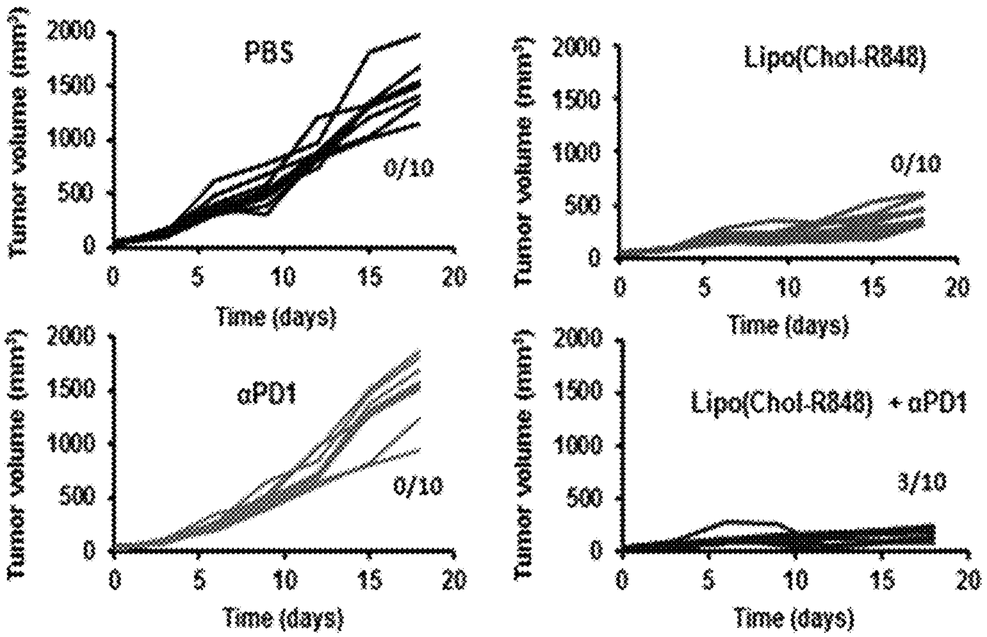
Figure 23C:
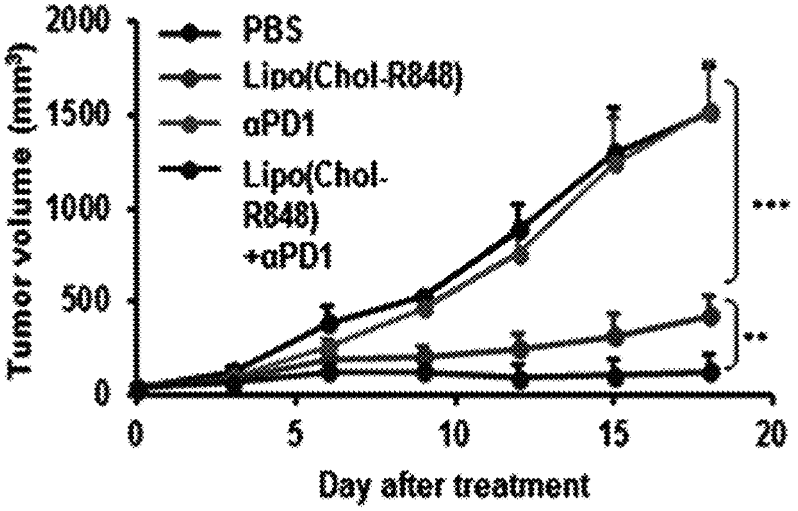
Figure 23D:
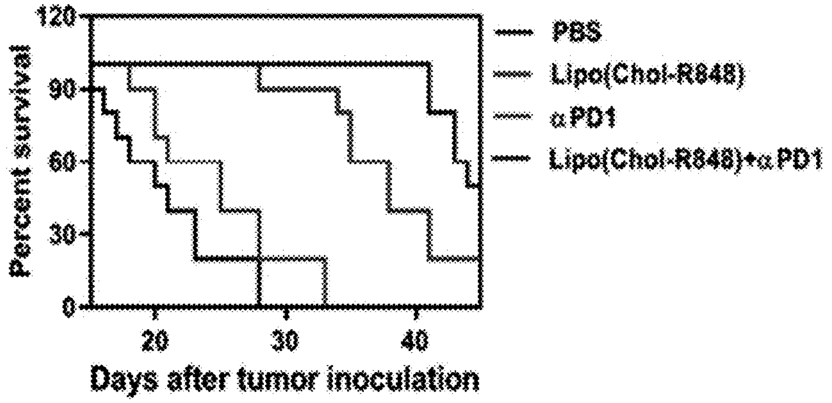

As shown in FIG. 21, in the case of the B16-OVA animal model, it was confirmed that tumor growth is considerably inhibited, and 6 or 7 tumor-free mice among 10 mice are observed in the experimental group co-administered an immune checkpoint inhibitor, indicating a high anticancer effect.

As shown in FIGS. 22A to 22E, in the case of the TC1 animal model, it was also confirmed that tumor growth is considerably inhibited and a survival rate is increased in the experimental group co-administered an immune checkpoint inhibitor. Moreover, it was confirmed that metastasis to the lungs was also inhibited.

As shown in FIGS. 23A-23D, in the case of the 4T1 animal model, it was also confirmed that tumor growth is inhibited and a survival rate is increased in the experimental group co-administered an immune checkpoint inhibitor.

6.3. Verification of Anticancer Effect of Co-Administration of Cholesterol-Toll-Like Receptor 7/8 Agonist Complex and Chemotherapeutic Agent To confirm an anticancer effect in the co-administration of the cholesterol-toll-like receptor 7/8 agonist complex and a chemotherapeutic agent, a 4T1 animal model was prepared in the same method as in Example 6.2, and doxorubicin or paclitaxel as a chemotherapeutic agent and a nanoliposome including the cholesterol-resiquimod complex were co-administered. In addition, after two weeks, a cancer size was measured. The result is shown in FIG. 24.

As shown in FIG. 24, compared to the group administered a chemotherapeutic agent alone, in the case of co-administration, it was confirmed that cancer growth was not only effectively inhibited, but the number of tumor-free mice also increased.

From the above results, since the toll-like receptor 7/8 agonist-cholesterol complex can be prevented from penetrating into blood, side effects of the conventional toll-like receptor 7/8 agonist can be considerably reduced, and cytotoxicity is not exhibited, it was confirmed that not only intracellular delivery efficacy does increases, but the degree of immune activity also increases due to effective separation from cholesterol compared to when a toll-like receptor 7/8 agonist is used alone. In addition, since it is based on cholesterol, the toll-like receptor 7/8 agonist-cholesterol complex may be easily prepared in the form of a nanoemulsion, nanoliposome or nanomicelle, and thus it is expected that the toll-like receptor 7/8 agonist may not only be widely used as an immune activation therapeutic agent, but also may increase an immune response of the antigen when used as an adjuvant in combination with an antigen. In addition, the toll-like receptor 7/8 agonist-cholesterol complex of the present disclosure induces immune activation of antigen-presenting cells (dendritic cells or macrophages), NK cells and T cells, and regulates the function of immune cells having an immunosuppressive action (regulatory T cells (Tregs), myeloid-derived suppressor cells (MDSCs), or M2 macrophages) in a tumor microenvironment, and thus it is expected that they can be used as a composition for various types of anticancer treatment. In addition, specially, since an anticancer effect may considerably increase due to a synergistic effect in co-administration with materials for anticancer treatment such as an immune checkpoint inhibitor and a chemotherapeutic agent, the toll-like receptor 7/8 agonist-cholesterol complex may also be used in co-administration with various anticancer therapeutic agents.

The toll-like receptor 7/8 agonist-cholesterol complex of the present disclosure is inactivated when administered into a body, but activated when separated from cholesterol in a tumor microenvironment and/or under a specific condition in cells. Therefore, it can not only reduce a side effect such as a non-specific hypersensitive immune response, but can also be prepared in various formulations because it is complexed with cholesterol, and also inhibits absorption into a blood vessel, thereby inhibiting a side effect such as a cytokine storm. In addition, since the toll-like receptor 7/8 agonist-cholesterol complex alone can exhibit an anticancer effect by effectively regulating immune cells, but also considerably increase an effect of co-administration with various cancer therapeutic agents and immunotherapeutic agents, the toll-like receptor 7/8 agonist-cholesterol complex is expected to be effectively and widely applied to treatment of various diseases to which the toll-like receptor agonist can be applied.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation.

Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A toll-like receptor 7/8 agonist-cholesterol complex, in which cholesterol is linked to an active site of a toll-like receptor 7/8 agonist, wherein the linkage is made in a separable form, and wherein the separable linkage is made by at least one selected from the group consisting of a carbamate, a disulfide, an ester, a peptide, an azide, and a combination thereof, wherein the toll-like receptor 7/8 agonist is selected from the group consisting of imiquimod, resiquimod, dactolisib, gardiquimod, sumanirole, motolimod, vesatolimod, loxoribine, SM360320, CL264, 3M-003, IMDQ, and Compound 54.

2. The complex of claim 1, wherein the separable linkage is cleaved in response to a tumor microenvironment, a temperature, an endosomal enzyme, a lysosomal enzyme, or pH in cells, and the active site of the toll-like receptor 7/8 agonist is exposed by cleavage of the separable linkage, thereby recovering a kinetic function of the toll-like receptor 7/8 agonist within 4 days.

3. A nanoparticle composition comprising the toll-like receptor 7/8 agonist-cholesterol complex of claim 1.

4. The nanoparticle composition of claim 3, wherein the nanoparticle comprises at least one selected from the group consisting of a nanoliposome, a nanoemulsion, a nanomicelle, a solid nanoparticle, and a polymer nanoparticle.

5. An adjuvant composition comprising the toll-like receptor 7/8 agonist-cholesterol complex of claim 1 as an active ingredient.

6. A vaccine composition comprising the adjuvant composition of claim 5 and an antigen.

7. The vaccine composition of claim 6, wherein the antigen is selected from the group consisting of a protein, a recombinant protein, a glycoprotein, a gene, a peptide, a polysaccharide, a lipopolysaccharide, a polynucleotide, a cell, a cell lysate, a bacterium, and a virus.

8. A composition for controlling an immune function or preventing or treating a cancer, comprising the toll-like receptor 7/8 agonist-cholesterol complex of claim 1 as an active ingredient.

9. The composition of claim 8, wherein the composition activates at least one immune cell selected from the group consisting of an antigen-presenting cell, a natural killer cell and a T cell.

10. The composition of claim 8, wherein the composition regulates a function of at least one immune cell selected from the group consisting of a regulatory T cell, a myeloid-derived suppressor cell, and a M2 macrophage.

11. The composition of claim 8, further comprising a chemotherapeutic agent, an immune checkpoint inhibitor, or a combination thereof.

12. The composition of claim 8, wherein the composition inhibits cancer proliferation, metastasis, recurrence of cancer, or resistance to anticancer therapy.

13. The complex of claim 1, wherein the complex is prepared by the following method:

chemically bonding a cholesterol to an amine group of an active site of the toll-like receptor 7/8 agonist using a linker which is made in a separable form.

14. The complex of claim 13, wherein the bonding comprises:

preparing a disulfide cross-linker by dissolving 2-hydroxyethyl disulfide in a tetrahydrofuran to prepare a solution;

adding and dissolving the solution in a toluene solution, and adding and dissolving N-hydrosuccinimide and triethylamine in the toluene solution;

preparing a disulfide-cholesterol cross-linker by mixing and reacting the disulfide cross-linker and the cholesterol; and mixing and reacting the disulfide-cholesterol cross-linker and the toll-like receptor 7/8 agonist.

* * * * *